United States Patent
Lynch

(10) Patent No.: US 12,288,736 B2
(45) Date of Patent: Apr. 29, 2025

(54) SENSOR PACKAGE, ARTICLE COMPRISING THE SAME AND MANUFACTURING METHOD THEREOF

(71) Applicant: Prevayl Innovations Limited, Wilmslow (GB)

(72) Inventor: Michael John Lynch, Manchester (GB)

(73) Assignee: Prevayl Innovations Limited, Wilmslow (GB)

( * ) Notice: Subject to any disclaimer, the term of this patent is extended or adjusted under 35 U.S.C. 154(b) by 119 days.

(21) Appl. No.: 17/772,242

(22) PCT Filed: Nov. 26, 2020

(86) PCT No.: PCT/GB2020/053005
§ 371 (c)(1),
(2) Date: Apr. 27, 2022

(87) PCT Pub. No.: WO2021/105676
PCT Pub. Date: Jun. 3, 2021

(65) Prior Publication Data
US 2022/0384315 A1    Dec. 1, 2022

(30) Foreign Application Priority Data

Nov. 28, 2019 (GB) .................................. 1917331
Mar. 24, 2020 (GB) .................................. 2004244
Mar. 24, 2020 (GB) .................................. 2004245

(51) Int. Cl.
*H01L 23/495* (2006.01)
*A61B 5/318* (2021.01)
(Continued)

(52) U.S. Cl.
CPC .......... *H01L 23/4951* (2013.01); *A61B 5/318* (2021.01); *H01L 21/4846* (2013.01);
(Continued)

(58) Field of Classification Search
CPC ............................ H01L 23/4951; A61B 5/318
See application file for complete search history.

(56) References Cited

U.S. PATENT DOCUMENTS 6,397,280 B1   5/2002   Nitschke et al.
6,646,336 B1   11/2003  Marmaropoulos et al.
(Continued)

FOREIGN PATENT DOCUMENTS

CN   110123305 A   8/2019
DE   19647668 A1   5/1998
(Continued)

OTHER PUBLICATIONS

Examination Report received for GB Application No. 2004244.6, mailed on Sep. 15, 2023, 2 pages.
(Continued)

*Primary Examiner* — Eugene Lee
(74) *Attorney, Agent, or Firm* — Haley Guiliano LLP

(57) ABSTRACT

The sensor semiconductor package (100) comprises a die pad (101), external connection terminals (103), semiconductor chip 105 and sealing member. The semiconductor chip (105) is located on a top surface of the die pad (101) and is electrically connected with the external connection terminals (103) and the die pad (101). The sealing member covers the die pad (101), the external connection terminals (103) and the semiconductor chip (105) and exposes an outer terminal (115) of each of the external connection terminals (103) and an outer contact surface (117) of the die pad (101). The outer contact surface (117) of the die pad (101) forms an electrode (117) of the sensor semiconductor package (100). The article comprises the sensor semiconductor package (100). The method manufactures the sensor semiconductor package (100) and the article.

18 Claims, 13 Drawing Sheets

(51) Int. Cl.
  *H01L 21/48* (2006.01)
  *H01L 23/31* (2006.01)
  *H01L 23/498* (2006.01)
  *H01L 23/522* (2006.01)

(52) U.S. Cl.
  CPC .... *H01L 23/3142* (2013.01); *H01L 23/49811* (2013.01); *H01L 23/522* (2013.01)

(56) References Cited

U.S. PATENT DOCUMENTS

| | | |
|---|---|---|
| 6,943,061 B1 | 9/2005 | Sirinorakul et al. |
| 8,022,522 B1 | 9/2011 | Liou et al. |
| 9,138,191 B1 | 9/2015 | Kaskoun et al. |
| 10,485,475 B1* | 11/2019 | Miller ............... A61B 5/1455 |
| 11,534,615 B2 | 12/2022 | Briscoe et al. |
| 11,571,143 B2 | 2/2023 | Katz et al. |
| 2003/0023777 A1 | 1/2003 | Fields et al. |
| 2003/0211797 A1 | 11/2003 | Hill et al. |
| 2007/0152812 A1 | 7/2007 | Wong et al. |
| 2007/0164409 A1 | 7/2007 | Holland |
| 2007/0173083 A1 | 7/2007 | Kopplin |
| 2007/0214872 A1 | 9/2007 | Ammann et al. |
| 2010/0036209 A1 | 2/2010 | Ferren et al. |
| 2013/0106673 A1* | 5/2013 | McCormack ......... H01L 23/495 343/893 |
| 2014/0070957 A1 | 3/2014 | Longinotti-Buitoni et al. |
| 2014/0135593 A1 | 5/2014 | Jayalth et al. |
| 2014/0269812 A1 | 9/2014 | Deutscher et al. |
| 2015/0015249 A1 | 1/2015 | Ausserlechner et al. |
| 2017/0053856 A1 | 2/2017 | Luan |
| 2017/0181703 A1 | 6/2017 | Kaib et al. |
| 2017/0264978 A1 | 9/2017 | Leftly et al. |
| 2018/0090449 A1 | 3/2018 | Jeong et al. |
| 2018/0107244 A1 | 4/2018 | Fujie et al. |
| 2018/0138616 A1 | 5/2018 | Dumont |
| 2018/0184975 A1 | 7/2018 | Kaasinen et al. |
| 2018/0269850 A1* | 9/2018 | Ito ..................... H03H 9/02551 |
| 2018/0295720 A1 | 10/2018 | Aleksov et al. |
| 2018/0345079 A1* | 12/2018 | Lindman ............ A61B 5/0022 |
| 2019/0076082 A1 | 3/2019 | Poutiatine et al. |
| 2019/0096833 A1* | 3/2019 | Lim ..................... H01L 24/19 |
| 2019/0133474 A1 | 5/2019 | Longinotti-Buitoni |
| 2019/0166089 A1 | 5/2019 | Schmitz et al. |
| 2020/0004027 A1 | 1/2020 | Grootjans et al. |
| 2020/0273838 A1* | 8/2020 | Williams ............ H01L 23/3114 |
| 2020/0361764 A1* | 11/2020 | Van Der Avoort ... G01L 9/0073 |

FOREIGN PATENT DOCUMENTS

| | | |
|---|---|---|
| DE | 10251900 A1 | 5/2004 |
| EP | 3370367 A1 | 9/2018 |
| GB | 2555592 A | 5/2018 |
| GB | 2589567 A | 6/2021 |
| GB | 2592391 A | 9/2021 |
| GB | 2593479 A | 9/2021 |
| GB | 2593674 A | 10/2021 |
| WO | 2011/095857 A1 | 8/2011 |
| WO | 2016/051268 A1 | 4/2016 |
| WO | 2016/054057 A1 | 4/2016 |
| WO | WO 2019020550 | 1/2019 |
| WO | 2019/134031 A2 | 7/2019 |
| WO | WO 2019197892 | 10/2019 |
| WO | 2021/105676 A1 | 6/2021 |

OTHER PUBLICATIONS

GB Search Report dated Apr. 6, 2020 of GB Application 1917331.9.
GB Search Report dated Sep. 16, 2020 of GB Application 2004244.6.
GB Search Report dated Sep. 16, 2020 of GB Application 2004245.3.
International Search Report and Written Opinion of PCT/GB2020/053005 dated Feb. 22, 2021.
British Search Report, dated Aug. 19, 2020, issued in GB Pat. App. No. 1917334.3 (3 pages).
British Search Report, dated Aug. 6, 2020, issued in GB Pat. App. No. 1917332.7 (4 pages).
British Search Report, dated Mar. 10, 2021, issued in GB Pat. App. No. 1917342.6 (4 pages).
Chew, et al., "Electrical Power Monitoring System Using Thermochron Sensor and 1-Wire Communication Protocol", 4th IEEE International Symposium on Electrical Design, pp. 549-554 (2008).
Datasheet DS2422, Maxim Integrated, 2010, pp. 1-49, retrieved from the Internet: URL: https://datasheets.maximintegrated.com/en/ds/DS2422.pdf [retrieved on Jul. 24, 2017].
Examination Report received in GB2002716.5 mailed Jun. 30, 2022.
Examination Report received in GB2002716.5 mailed Mar. 18, 2022.
Examination Report received in GB2002716.5 mailed Mar. 23, 2021.
Examination Report received in GB2002716.5 mailed Mar. 9, 2021.
Examination Report received in GB2002716.5 mailed May 16, 2022.
International Search Report and Written Opinion received for PCT Patent Application No. PCT/GB2020/053006, mailed on Feb. 26, 2021, 14 pages.
International Search Report and Written Opinion, dated Apr. 7, 2021, issued in Int'l. App. No. PCT/GB2020/053010 (23 pages).
International Search Report and Written Opinion, dated Apr. 7, 2021, issued in Int'l. App. No. PCT/GB2020/053012 (24 pages).
International Search Report and Written Opinion, dated Feb. 18, 2021, issued in Int'l. App. No. PCT/GB2020/053009 (15 pages).
International Search Report and Written Opinion, dated Feb. 25, 2021, issued in Int'l. App. No. PCT/GB2020/053015 (9 pages).
International Search Report and Written Opinion, dated Feb. 26, 2021, issued in Int'l. App. No. PCT/GB2020/053006 (17 pages).
International Search Report received in PCT/GB2021/050449 mailed May 11, 2021.
NPL Search (Apr. 6, 2023).
Search and Examination Report received in GB2002716.5 mailed Aug. 18, 2020.
Search Report received in GB2002717.3 mailed Aug. 17, 2020.
Silicon Labs: "I2C Humidity and Temperature Sensor", pp. 1-36, Aug. 1, 2016, retrieved from the Internet: URL: https://cdn-learn.adafruit.com/assets/assets/000/035/931/original/Support_Documents_technicalDocs_Si7021-A20.pdf [retrieved on Jun. 5, 2019].
Written Opinion received in PCT/GB2021/050449 mailed May 11, 2021.
U.S. Appl. No. 17/779,481, filed May 24, 2022, Michael John Lynch.
U.S. Appl. No. 17/779,483, filed May 24, 2022, Michael John Lynch.
U.S. Appl. No. 17/779,486, filed May 24, 2022, Michael John Lynch.
U.S. Appl. No. 17/796,949, filed Aug. 2, 2022, Michael John Lynch.

\* cited by examiner

SENSOR PACKAGE, ARTICLE COMPRISING THE SAME AND MANUFACTURING METHOD THEREOF

CROSS-REFERENCE TO RELATED APPLICATIONS

This application is a national stage application under 35 U.S.C. § 371 of International Application PCT/GB2020/053005, filed Nov. 26, 2020, which claims priority of GB Patent Applications 1917331.9, filed Nov. 28, 2019, 2004244.6, filed Mar. 24, 2020, and 2004245.3, filed Mar. 24, 2020. The disclosure of which are hereby incorporated by reference herein in their entireties.

BACKGROUND

The present invention is directed towards a semiconductor package, article, and method. The present invention is directed, in particular towards a semiconductor package that performs sensing functions which will otherwise be referred to as a sensor semiconductor package.

Referring to FIG. 1A there is shown a sensor 10 according to existing implementations. The sensor 10 comprises a controller 11 and a pair of electrodes 13. The pair of electrodes 13 are connected to the controller 11 by wires 15. The controller 11 may be in the form of a semiconductor package.

It is an objective of the present disclosure to overcome at least some of the problems associated with the prior art, whether explicitly discussed herein or otherwise.

SUMMARY

According to the present disclosure there is provided a sensor semiconductor package, article and method as set forth in the appended claims. Other features of the invention will be apparent from the dependent claims, and the description which follows.

According to a first aspect of the disclosure, there is provided a sensor semiconductor package. The sensor semiconductor package comprises: at least one die pad; a plurality of external connection terminals; a semiconductor chip electrically connected with the plurality of external connection terminals and the at least one die pad; and a sealing member covering the at least one die pad, the plurality of external connection terminals and the semiconductor chip and exposing an outer terminal of each of the plurality of external connection terminals and an outer contact surface of the at least one die pad, wherein the outer contact surface of the at least one die pad forms an electrode of the sensor semiconductor package. The semiconductor chip may be located on a top surface of the at least one die pad.

The present disclosure provides a sensor in the form of a semiconductor package. The electrode(s) of the sensor are incorporated into the semiconductor package. Beneficially, this means that the form factor of the sensor is reduced compared to existing sensors which provide electrodes physically spaced apart from a controller of the sensor. The sensor semiconductor package utilizes the exposed outer contact surface of the die pad as the electrode for the sensor. Die pads are provided in existing semiconductor packages as heat sinks and are not electrically connected to the semiconductor chip. In this way a self-contained semiconductor package for performing sensing functions using an integral electrode is provided utilizing existing semiconductor package structures, and requiring minimal changes to existing, established, semiconductor package manufacturing techniques.

The plurality of external connection terminals may be located around the at least one die pad. The sensor semiconductor package may have a rectangular bottom surface. The plurality of external connection terminals may be provided along one or more sides of the rectangular bottom surface. The semiconductor chip may be attached to the top surface of the at least one die pad by an adhesive. The die pad may be located in the centre of the bottom surface of the sensor semiconductor package but this is not required in all aspects of the present disclosure. The die pad may be offset from the centre for example.

At least one wire may extend from the semiconductor chip to connect the semiconductor chip to the at least one die pad. A plurality of wires may extend from the semiconductor chip to connect the semiconductor chip to the plurality of external connection terminals.

The semiconductor chip may be arranged to receive a measurement signal from the die pad, and optionally perform at least one processing operation on the receive measurement signal.

The semiconductor chip may be arranged to send and/or receive data via at least one of the external connection terminals. At least one of the external connection terminals may function as a ground, or return, for the semiconductor chip.

The at least one die pad may comprise a first die pad and a second die pad. The semiconductor chip may be located on a top surface of one or both of the first die pad and the second die pad. The semiconductor chip may be (separately) electrically connected to the first die pad and the second die pad. The sealing member may expose an outer contact surface of the first die pad. The sealing member may expose an outer contact surface of the second die pad. The outer contact surface of the first die pad may form a first electrode of the sensor semiconductor package. The outer contact surface of the second die pad may form a second electrode of the sensor semiconductor package.

The sensor semiconductor package may be a biosensor (biosignal sensor) semiconductor package. The electrode of the biosensor semiconductor package may be for monitoring a biosignal of a living body. The electrode of the biosensor semiconductor package may be for monitoring a bioelectrical signal of the living body. The electrode of the biosensor semiconductor package may be for monitoring a biopotential signal of the living body. The electrode of the biosensor semiconductor package may be for monitoring a bioimpedance signal of the living body. The biosensor semiconductor package may be an electrocardiography semiconductor sensor package. The biosensor semiconductor package may be an electromyography semiconductor sensor package.

According to a second aspect of the disclosure, there is provided an article comprising the sensor semiconductor package of the first aspect of the disclosure. The article may be a wearable article. The wearable article may be a garment. The present disclosure is not limited to wearable articles. The sensor semiconductor packages disclosed herein may be incorporated into other forms of devices such as user electronic devices (e.g. mobile phones). In addition, the sensor semiconductor packages as disclosed herein may be incorporated into any form of textile article. Textile articles may include upholstery, such as upholstery that may be positioned on pieces of furniture, vehicle seating, as wall or ceiling decor, among other examples.

According to a third aspect of the disclosure, there is provided a method for manufacturing a sensor semiconductor package. The method comprises providing at least one die pad and a plurality of external connection terminals; providing a semiconductor chip; electrically connecting the semiconductor chip to the plurality of external connection terminals and the at least one die pad; forming a sealing member covering the die pad, the plurality of external connection terminals and the semiconductor surface and exposing an outer terminal of each of the plurality of external connection terminals and an outer contact surface of the at least one die pad, wherein the outer contact surface of the at least one die pad forms an electrode of the sensor semiconductor package. The method may comprise locating the semiconductor chip on a top surface of the at least one die pad prior to electrically connecting the semiconductor chip to the at least one die pad.

Advantageously, the present disclosure provides a method for manufacturing a sensor semiconductor package which requires minimal modification to existing semiconductor package manufacturing techniques. In this way, the sensor semiconductor package according to the present disclosure is able to be manufactured rapidly, at scale, and at low cost.

The method may be for manufacturing a plurality of sensor semiconductor packages. The method may comprise providing a lead frame comprising a plurality of regions arranged to be separated from one another to provide the plurality of semiconductor packages. Each of the plurality of regions may comprise at least one die pad and a plurality of external connection terminals. The method may further comprise providing a plurality of semiconductor chips, and, for each of the regions, locating a semiconductor chip on a top surface of the at least one die pad. The method may further comprise, for each of the regions, electrically connecting the semiconductor chip to the plurality of external connection terminals and the at least one die pad. The method may further comprise, for each of the regions, forming a sealing member covering the die pad, the plurality of external connection terminals and the semiconductor surface and exposing an outer terminal of each of the plurality of external connection terminals and an outer contact surface of the at least one die pad, wherein the outer contact surface of the at least one die pad forms an electrode of the sensor semiconductor package. The method may further comprise separating the plurality of regions from one another to form the plurality of sensor semiconductor packages.

According to a fourth aspect of the disclosure, there is provided a method of manufacturing an article. The method comprises providing a textile material; providing a sensor semiconductor package according to the first aspect of the disclosure; and attaching the sensor semiconductor package to the textile material.

According to a fifth aspect of the disclosure, there is provided an article comprising: a textile material, the textile material comprising a first electrically conductive yarn and a second electrically conductive yarn, the first electrically conductive yarn and the second electrically conductive yarn extending along at least part of the length of the textile material; and a sensor semiconductor package comprising: a first external connection terminal; a second external connection terminal; a semiconductor chip electrically connected to the first external connection terminal and the second external connection terminal; and a sealing member covering the first and second external connection terminals and the semiconductor chip and exposing an outer terminal of each of the first and second external connection terminals, wherein the sensor semiconductor package is located on the textile material, and wherein the first electrically conductive yarn is electrically connected to the first external connection terminal, and wherein the second electrically conductive yarn is electrically connected to the second external connection terminal.

Beneficially, the present disclosure provides a textile article with sensor semiconductor packages that are electrically connected via electrically conductive yarns of the textile material. This provides an effective mechanism for integrating and electrically connecting sensor semiconductor packages in an article.

The first electrically conductive yarn and the second electrically conductive yarn may extend substantially parallel to one another. The first external connection terminal and the second external connection terminal may be located on opposite sides of the sensor semiconductor package such that the sensor semiconductor package is disposed between the first electrically conductive yarn and the second electrically conductive yarn.

A plurality of first external connection terminals may be electrically connected to the first electrically conductive yarn. A plurality of second external connection terminals may be electrically connected to the second electrically conductive yarn.

The first and second electrically conductive yarns may be stitched, woven or knitted into the textile material. The first and second electrically conductive yarns may be stitched into the textile material using a twin-needle stich. Beneficially, using a twin-needle stitch enables the first and second electrically conductive yarns to be integrated into the textile material in a single stitching operation which also ensures that the yarns are substantially parallel to one another.

The first external connection terminal may be soldered to the first electrically conductive yarn. The second external connection terminal may be soldered to the second electrically conductive yarn. Soldering may additionally help mechanically connect the sensor semiconductor package to the textile and thus may provide additional mechanical advantage.

The first electrically conductive yarn may be a bidirectional line for the article. The semiconductor chip of the sensor semiconductor package may be arranged to send and/or receive data over the bidirectional line. The bidirectional line may be a single-wire bidirectional line. The semiconductor chip of the sensor semiconductor package may send and/or receive data over the singe-wire bidirectional line using a single-wire communication protocol.

The second electrically conductive yarn may be a return (i.e. a ground) line for the article. The semiconductor chip of the sensor semiconductor package may be connected to ground via the return line.

The electrical connection of the first and second external connection terminals to the first and second electrically conductive yarns may mechanically connect the sensor semiconductor package to the textile material. In this way, an additional adhesive may not be required to attach the sensor semiconductor package to the textile material or an adhesive connection may be strengthened by the electrically connection of the external connection terminals to the conductive yarns.

The sensor semiconductor package may comprise an electrode (or a plurality of electrodes) electrically connected to the semiconductor chip.

The sensor semiconductor package may further comprise a die pad. The semiconductor chip may be located on a top surface of the die pad. The sealing member may cover the die pad and may expose an outer contact surface of the die pad. The sensor semiconductor package may be electrically connected to the die pad, and the outer contact surface of the die pad may form an electrode of the sensor semiconductor package. At least one wire may extend from the semiconductor chip to connect the semiconductor chip to the die pad. A plurality of wires may extend from the semiconductor chip to connect the semiconductor chip to the plurality of external connection terminals.

The semiconductor chip may be arranged to receive a measurement signal from the die pad, and optionally perform at least one processing operation on the receive measurement signal. The semiconductor chip may be attached to the top surface of the at least one die pad by an adhesive.

The sensor semiconductor package may be a first sensor semiconductor package, and wherein the article may further comprises a second sensor semiconductor package. The second sensor semiconductor package may comprise: a first external connection terminal; a second external connection terminal; a semiconductor chip electrically connected to the first external connection terminal and the second external connection terminal; and a sealing member covering the first and second external connection terminals and the semiconductor chip and exposing an outer terminal of each of the first and second external connection terminals.

The second sensor semiconductor package may be located on the textile material. The first electrically conductive yarn may be electrically connected to the first external connection terminal of the second sensor semiconductor package. The second electrically conductive yarn may be electrically connected to the second external connection terminal of the second sensor semiconductor package.

The article may further comprise an electronics module. The electronics module may comprise a power source, a processor and a memory. The electronics module may be arranged to be electrically connected to the first and second electrically conductive pathways and may further arranged to communicate with the sensor semiconductor package via the first and second electronically conductive pathways. The electronics module may be removable from the article. The article may comprise an electronics module holder for at least temporarily holding the electronics module.

The article may be a wearable article. The wearable article may be a garment.

The sensor semiconductor package may be a biosensor (biosignal sensor) semiconductor package for monitoring a biosignal of a living body. The biosignal may be one or more of a bioelectrical signal, a biopotential signal, and a bioimpedance signal of the living body. The biosensor semiconductor package may be an electrocardiography semiconductor sensor package and/or an electromyography semiconductor sensor package.

The sensor semiconductor package may comprise any or all of the features of the first aspect of the disclosure.

According to a sixth aspect of the disclosure, there is provided a method for manufacturing an article. The method comprises providing a textile material, the textile material comprising a first electrically conductive yarn and a second electrically conductive yarn, the first electrically conductive yarn and the second electrically conductive yarn extending along at least part of the length of the textile material. The method comprises providing a sensor semiconductor package comprising: a first external connection terminal; a second external connection terminal; a semiconductor chip electrically connected to the first external connection terminal and the second external connection terminal; and a sealing member covering the first and second external connection terminals and the semiconductor chip and exposing an outer terminal of each of the first and second external connection terminals. The method comprises locating the sensor semiconductor package on the textile material. The method comprises electrically connecting the first electrically conductive yarn is to the first external connection terminal. The method comprises electrically connecting the second electrically conductive yarn to the second external connection terminal.

Advantageously, the present disclosure provides a simple method for providing and electrically connecting sensor semiconductor packages on an article which simply requires the sensor semiconductor packages to be located on the textile material and electrically connected to conductive yarns of the textile material.

According to a seventh aspect of the present disclosure, there is provided a layer structure for application to a surface, the layer structure comprising: a first insulating layer; a second insulating layer; an electrically conductive layer positioned between the first insulating layer and the second insulating layer; a sensor semiconductor package provided on the electrically conductive layer, the sensor semiconductor package comprising: a first external connection terminal electrically connected to the electrically conductive layer; a second external connection terminal electrically connected to the electrically conductive layer; a semiconductor chip electrically connected to the first external connection terminal and the second external connection terminal; and a sealing member covering the first and second external connection terminals and the semiconductor chip and exposing an outer terminal of each of the first and second external connection terminals.

Advantageously, the present disclosure provides a layer structure which incorporates a sensor semiconductor package. The sensor semiconductor package is electrically connected to a conductive layer of the layer structure. Beneficially, this enables the effective and simple integration of sensor semiconductor packages onto an article. The layer structure can simply be attached to the article and an electronics module can be connected to the sensor semiconductor package via the conductive layer. Individually mounting a sensor semiconductor package on an article and connecting the sensor semiconductor package to an electronics module via a wire is thus avoided.

The layer structure may comprise a transfer layer. The first insulating layer may be provided on the transfer layer.

The layer structure may comprise an adhesive layer. The adhesive layer may be provided on the second insulating layer.

The first or second insulating layer may comprise one or more openings. These openings may serve as contact points to allow for an external electronics module to electrically connect to the conductive layer so as to communicate with the sensor semiconductor package.

The sensor semiconductor package may further comprise a die pad. The semiconductor chip may be located on a top surface of the die pad, and the sealing member may cover the die pad and expose an outer contact surface of the die pad. The first insulating layer may comprise an opening aligned with the outer contact surface of the die pad such that at least part of the outer contact surface of the die pad is not covered by the first insulating layer.

The electrically conductive layer may comprise an opening aligned with the outer contact surface of the die pad such that at least part of the outer contact surface of the die pad is not covered by the electrically conductive layer.

The sensor semiconductor package may be electrically connected to the die pad, and the outer contact surface of the die pad may form an electrode of the sensor semiconductor package.

At least one wire may extend from the semiconductor chip to connect the semiconductor chip to the at least one die pad. A plurality of wires may extend from the semiconductor chip to connect the semiconductor chip to the plurality of external connection terminals.

The semiconductor chip may be arranged to receive a measurement signal from the die pad, and optionally perform at least one processing operation on the receive measurement signal.

The semiconductor chip may be attached to the top surface of the at least one die pad by an adhesive.

The conductive layer may comprise a first conductive trace and a second conductive trace. The first conductive trace may be electrically connected to the first external connection terminal, and the second conductive trace may be electrically connected to the second external connection terminal.

The first conductive trace may be a bidirectional line for the article, and wherein the semiconductor chip of the sensor semiconductor package may be arranged to send and/or receive data over the bidirectional line.

The bidirectional line may be a single-wire bidirectional line, and wherein the semiconductor chip of the sensor semiconductor package sends and/or receives data over the singe-wire bidirectional line using a single-wire communication protocol.

The second conductive trace may be a return line for the article, and wherein the semiconductor chip of the sensor semiconductor package is connected to ground via the return line.

The first and second insulating layers may comprise non-conductive ink. The conductive layer may comprise conductive ink.

The sensor semiconductor package may comprise an electrode (or a plurality of electrodes) electrically connected to the semiconductor chip.

The sensor semiconductor package may be a first sensor semiconductor package. The layer structure may further comprise a second sensor semiconductor package. The second sensor semiconductor package may comprise: a first external connection terminal; a second external connection terminal; a semiconductor chip electrically connected to the first external connection terminal and the second external connection terminal; and a sealing member covering the first and second external connection terminals and the semiconductor chip and exposing an outer terminal of each of the first and second external connection terminals.

The second sensor semiconductor package may be provided on the electrically conductive layer. The first and second external connection terminals of the second sensor semiconductor package may be electrically connected to the conductive layer.

The sensor semiconductor package may comprise any or all of the features of the first aspect of the disclosure.

According to an eighth aspect of the disclosure, there is provided n article comprising the layer structure as of the seventh aspect of the disclosure, wherein the layer structure is attached to a surface of the article.

The article may further comprise an electronics module. The electronics module may comprise a power source, a processor and a memory. The electronics module may be arranged to be electrically connected to the electrically conductive layer of the layer structure and may be further arranged to communicate with the sensor semiconductor package via the electrically conductive layer.

The electronics module may be removable from the article, optionally wherein the article comprises an electronics module holder for at least temporarily holding the electronics module. The electronics module holder may be a pocket of the article.

According to a ninth aspect of the disclosure, there is provided a method for manufacturing a layer structure. The method comprises printing non-conductive ink onto a transfer layer to produce a first insulating layer; printing an electrically conductive ink onto said first non-conductive printed ink layer to produce an electrically conductive layer; providing a sensor semiconductor package, wherein the sensor semiconductor package comprises: a first external connection terminal; a second external connection terminal; a semiconductor chip electrically connected to the first external connection terminal and the second external connection terminal; and a sealing member covering the first and second external connection terminals and the semiconductor chip and exposing an outer terminal of each of the first and second external connection terminals; positioning the sensor semiconductor package on the electrically conductive layer such that the electrically conductive layer is electrically connected to the first and second external connection terminals; and printing non-conductive ink over said electrically conductive layer to produce a second insulating layer.

The method may further comprise applying an adhesive over the second insulating layer to produce an adhesive layer.

According to a tenth aspect of the disclosure, there is provided a method for manufacturing an article, the method comprising: providing a layer structure according to the seventh aspect of the disclosure; and attaching the layer structure to a surface of the article.

BRIEF DESCRIPTION OF THE DRAWINGS

Examples of the present disclosure will now be described with reference to the accompanying drawings, in which.

DETAILED DESCRIPTION

Figure 1A:
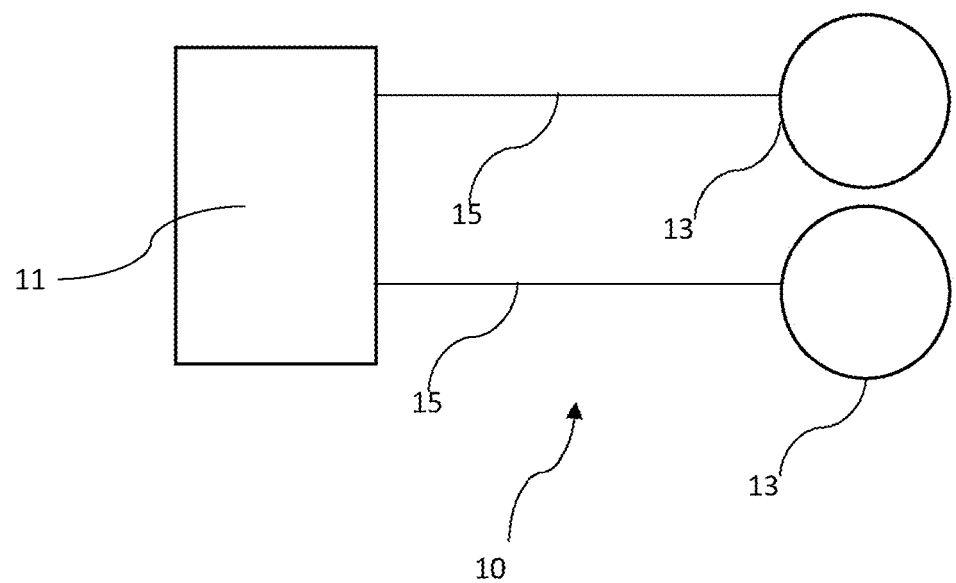
FIG. 1A is schematic diagram of an example sensor according to a prior art implementation.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise.

"Wearable article" as referred to throughout the present disclosure may refer to any form of electronic device which may be worn by a user such as a smart watch, necklace, bracelet, or glasses. The wearable article may be a textile article. The wearable article may be a garment. The garment may refer to an item of clothing or apparel. The garment may be a top. The top may be a shirt, t-shirt, blouse, sweater, jacket/coat, or vest. The garment may be a dress, brassiere, shorts, pants, arm or leg sleeve, vest, jacket/coat, glove, armband, underwear, headband, hat/cap, collar, wristband, stocking, sock, or shoe, athletic clothing, personal protection equipment, swimwear, wetsuit or drysuit The wearable article/garment may be constructed from a woven or a non-woven material. The wearable article/garment may be constructed from natural fibres, synthetic fibres, or a natural fibre blended with one or more other materials which can be natural or synthetic. The yarn may be cotton. The cotton may be blended with polyester and/or viscose and/or polyamide according to the particular application. Silk may also be used as the natural fibre. Cellulose, wool, hemp and jute are also natural fibres that may be used in the wearable article/garment. Polyester, polycotton, nylon and viscose are synthetic fibres that may be used in the wearable article/garment. The garment may be a tight-fitting garment. Beneficially, a tight-fitting garment helps ensure that the sensor devices of the garment are held in contact with or in the proximity of a skin surface of the wearer. The garment may be a compression garment. The garment may be an athletic garment such as an elastomeric athletic garment.

Figure 1B:
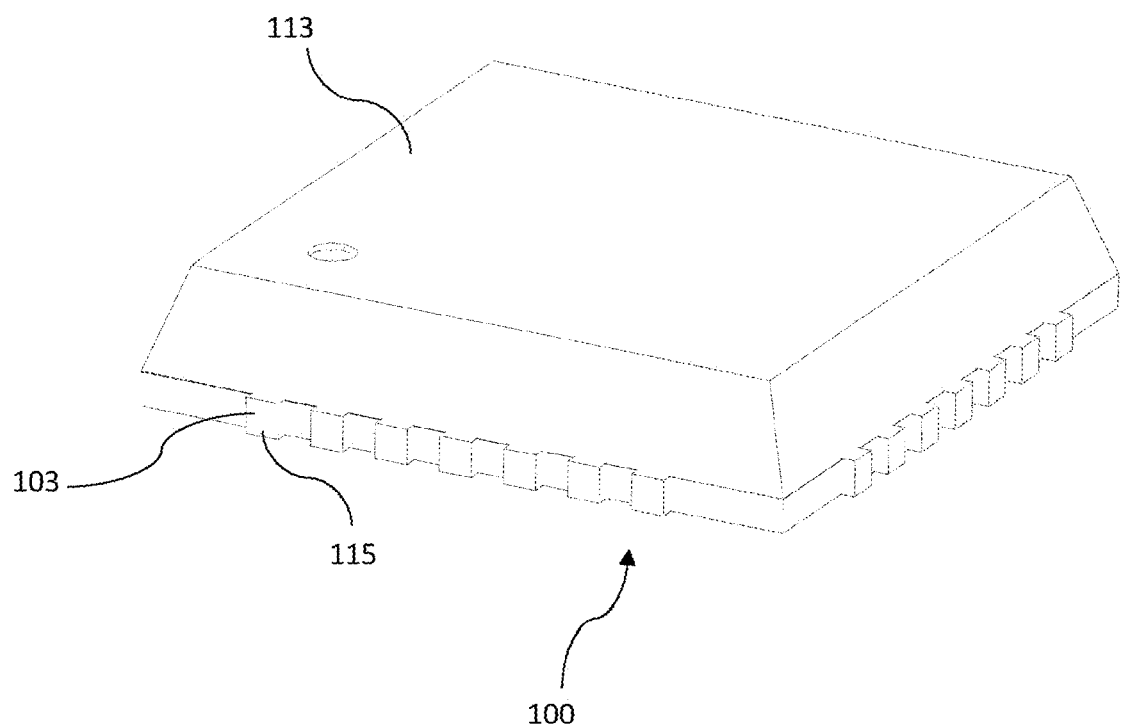
FIG. 1B is a perspective view of an example sensor semiconductor package according to aspects of the present disclosure.
Figure 2:
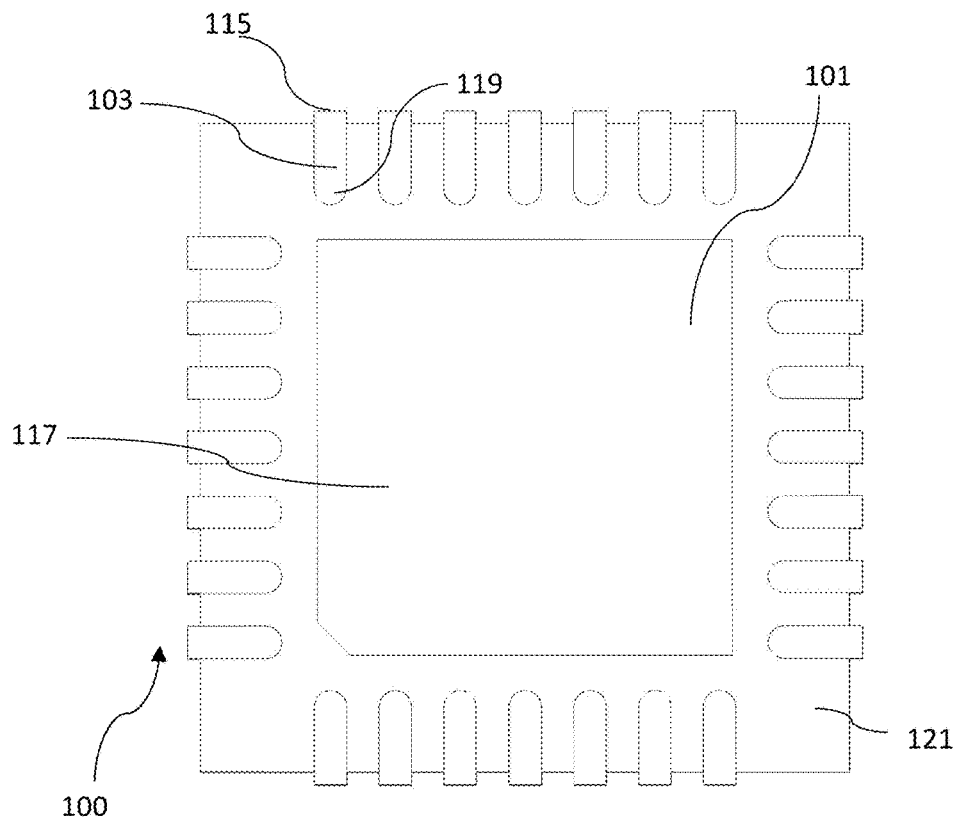
FIG. 2 is a bottom view of the sensor semiconductor package of FIG. 1B.
Figure 3:
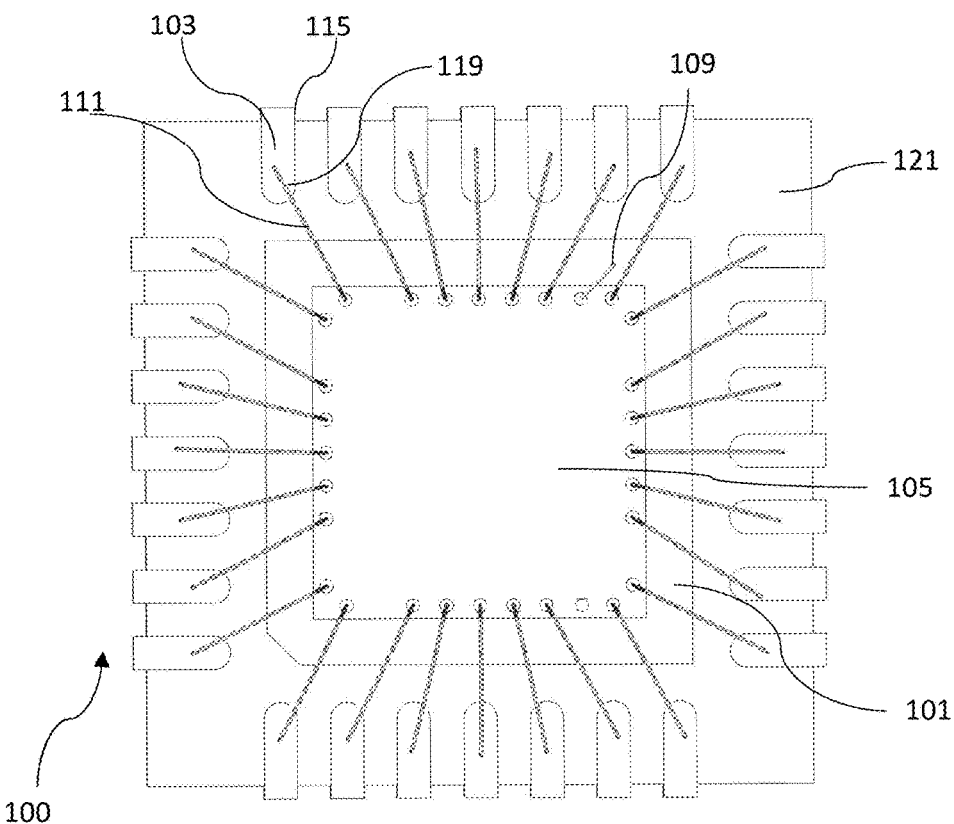
FIG. 3 is a plan view of the sensor semiconductor package of FIG. 1B with the sealing member removed.
Figure 4:
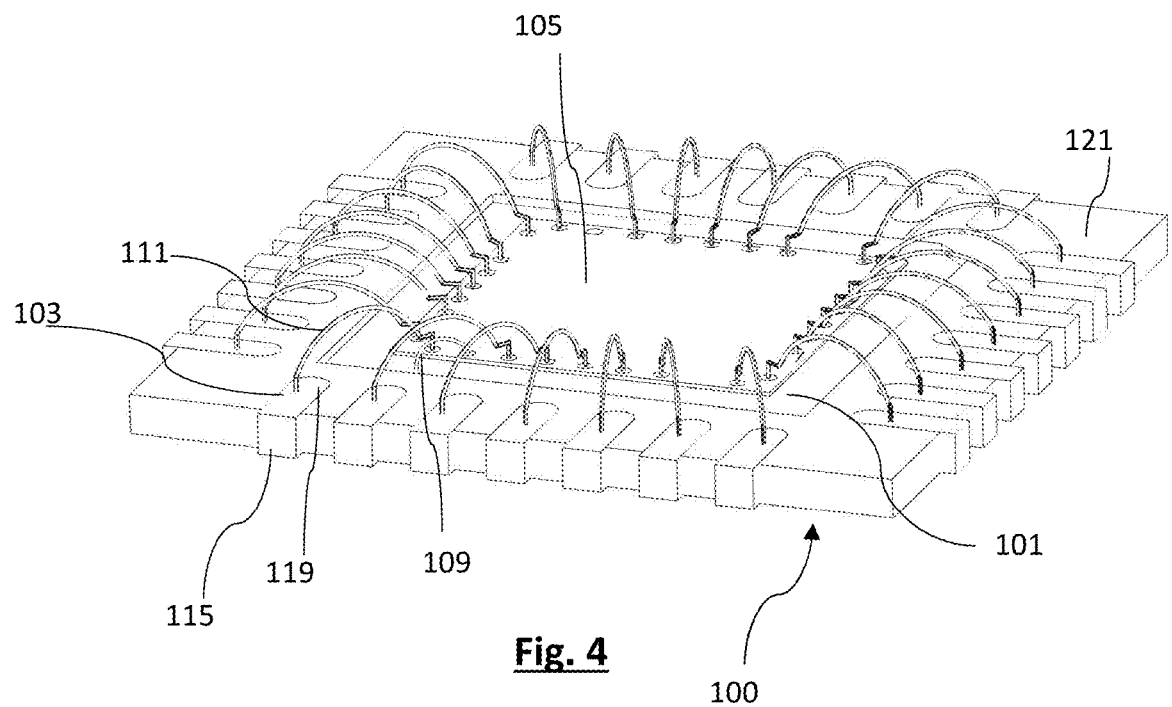
FIG. 4 is a perspective view of the sensor semiconductor package of FIG. 1B with the sealing member removed.
Figure 5:
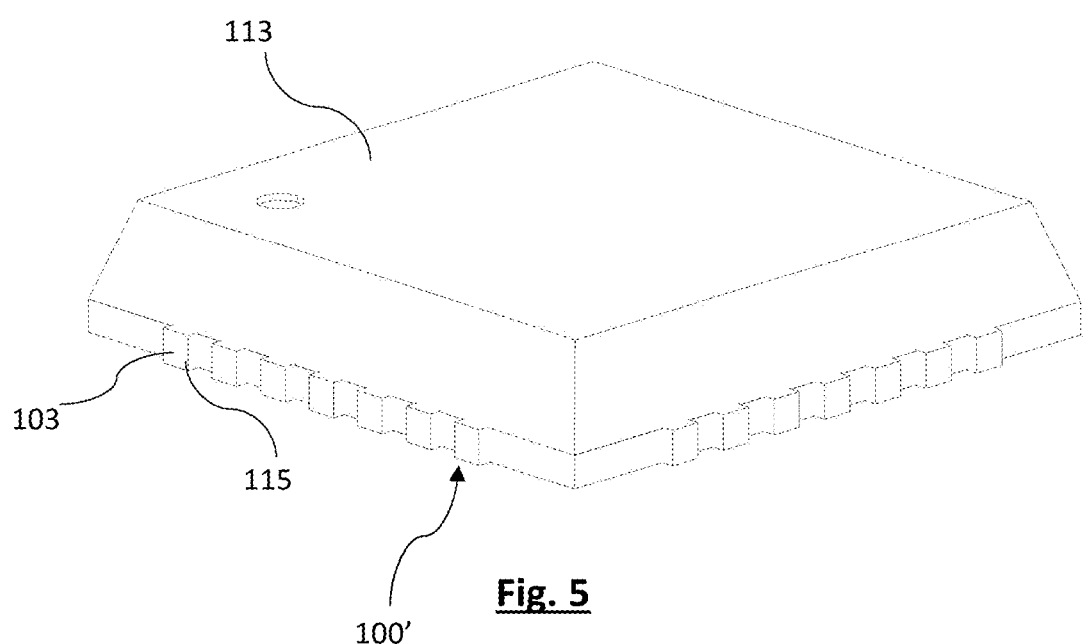
FIG. 5 is a perspective view of another example sensor semiconductor package according to aspects of the present disclosure.
Figure 6:
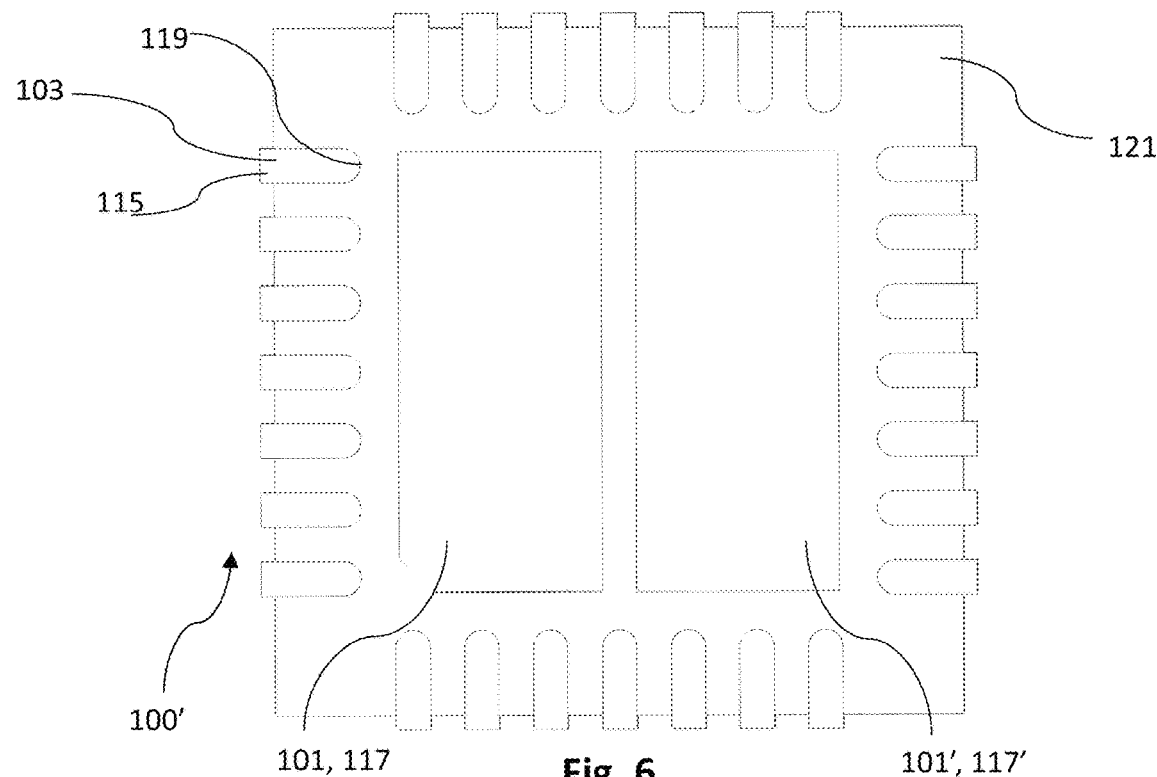
FIG. 6 is a bottom view of the sensor semiconductor package of FIG. 5.
Figure 7:
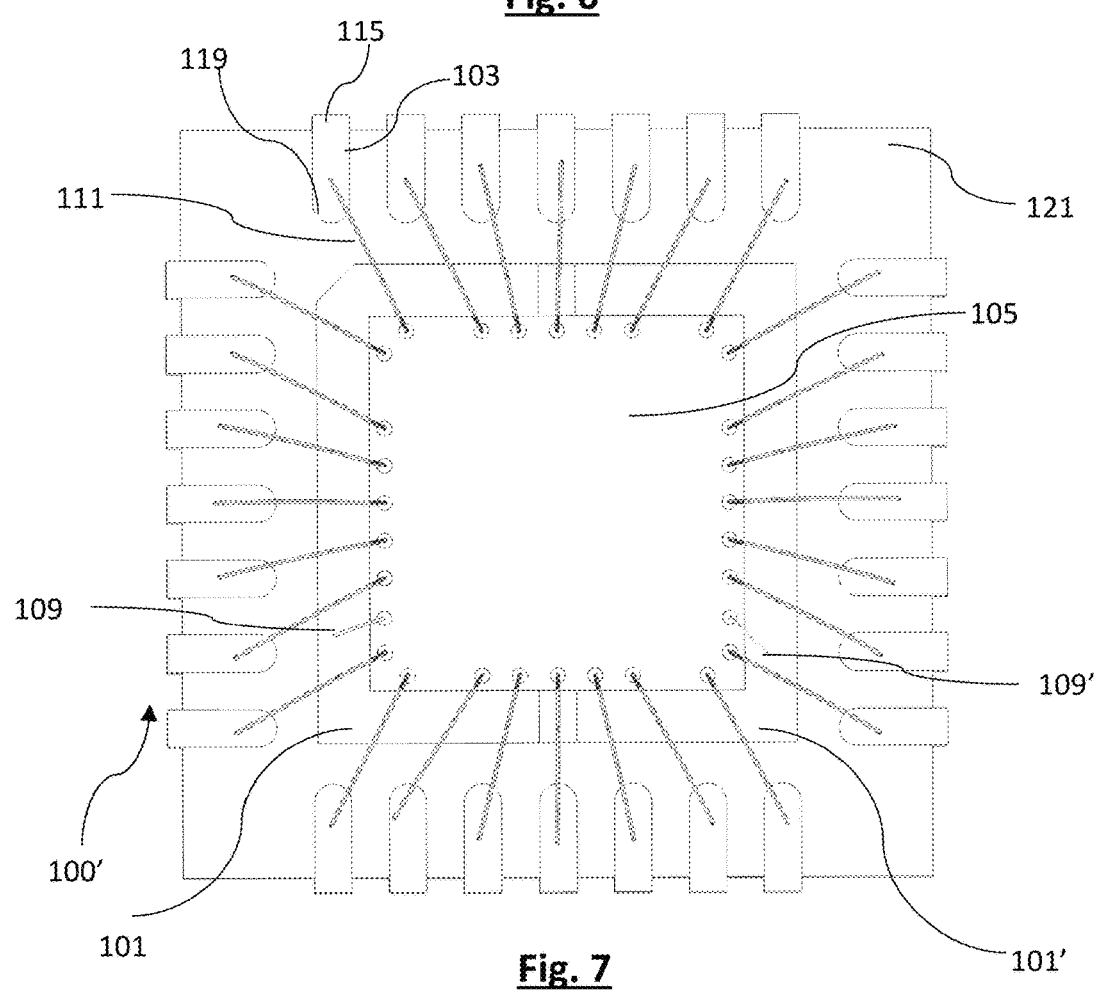
FIG. 7 is a plan view of the sensor semiconductor package of FIG. 5 with the sealing member removed.
Figure 8:
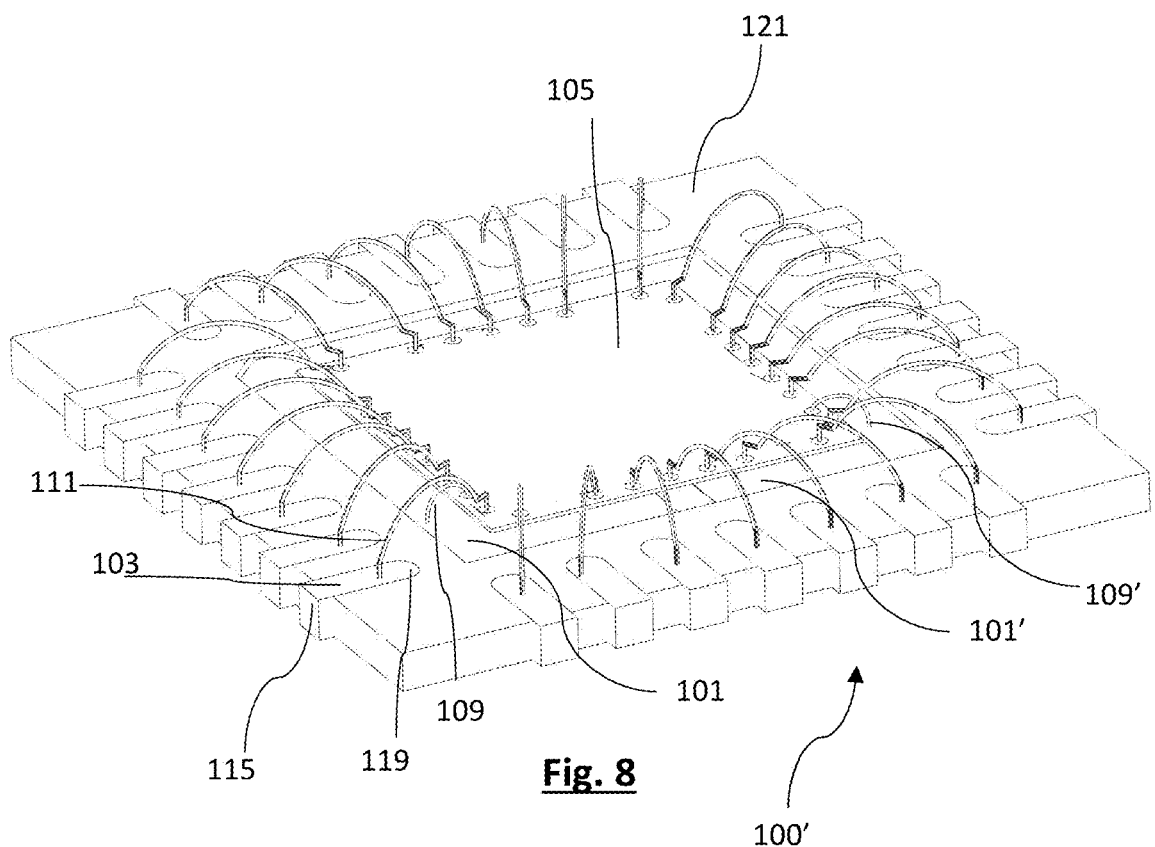
FIG. 8 is a perspective view of the sensor semiconductor package of FIG. 5 with the sealing member removed.

Referring to FIGS. 1B to 4, there is shown a sensor semiconductor package 100 according to aspects of the present disclosure. The sensor semiconductor package 100 comprises a single die pad 101 (FIG. 2). The die pad 101 is provided in a central region of the sensor semiconductor package 100. The sensor semiconductor package 100 comprises a plurality (twenty-eight in this example) of external connection terminals 103. The plurality of external connection terminals 103 are located around the die pad 101. The sensor semiconductor package 100 has a rectangular bottom surface 121. The plurality of external connection terminals 103 are provided along the four sides of the rectangular bottom surface 121. The die pad 101 is provided in the centre of the rectangular shape and has a substantially rectangular shape. In this specification, the term "rectangular" encompasses "square". The present disclosure is not limited to any particular number of external connection terminals, shape of semiconductor package, or shape of die pad.

The die pad 101 is formed of a conductive material. Generally, the die pad 101 is formed of a metal material having high mechanical strength, high electrical conductivity, and high resistance against corrosion. The metal material may also be desired to have high heat conductivity to enable the die pad 101 to transfer heat away from the semiconductor chip 105. This enables the die pad 101 to simultaneously function as an electrode and a heat sink. Example metal materials which may be used for the die pad 101 include copper-based materials such as copper alloys containing iron, phosphorous or the like. Other example metal materials which may be used for the die pad 101 include iron-based materials such as an iron alloy containing nickel or the like.

The external connection terminals 103 include an inner terminal 119 close to the die pad 101 and an outer terminal 115 further from the die pad 101 when compared to the inner terminal 119. The inner terminals 119 have a curved shape in this example, but that is not required in all aspects of the present disclosure. The external connection terminals 103 may, for example, have a rectangular shape. The outer terminals 115 may, for example, be curved or have a protruding portion. The external connection terminals 103 may have any structure as used in existing semiconductor packages. The external connection terminals 103 are generally preferred to be made of the same material as the die pad 101.

The sensor semiconductor package 100 further comprises a semiconductor chip 105 (FIG. 3) located on a top surface of the die pad 101 and electrically connected with the plurality of external connection terminals and the die pad. The semiconductor chip 105 is attached to the die pad 101 by an adhesive (not shown). A wire 109 extends from the semiconductor chip 105 to connect the semiconductor chip 105 to the die pad 101. A plurality of wires 111 extend from the semiconductor chip 105 to connect the semiconductor chip 105 to each of the external connection terminals 103. The wires 109, 111 may be formed of a material such as gold or copper. Other materials that provide the required conductivity and connectability may also be used.

The sensor semiconductor package 100 further comprises a sealing member 113 (FIG. 1B). The sealing member 113 covers the die pad 101, the plurality of external connection terminals 103, and the semiconductor chip 105. The sealing member 113 exposes an outer terminal 115 of each of the plurality of external connection terminals 103 and an outer contact surface 117 of the die pad 101. The outer contact surface 117 of the die pad 101 forms an electrode 117 of the sensor semiconductor package 100. The outer contact surface 117 of the die pad 101 is the exposed bottom surface 117 of the die pad 101 as best shown in FIG. 2. The outer terminals 115 of the plurality of external connection terminals 103 are the exposed bottom surfaces 115 and exposed side surfaces 115 of the external connection terminals 103 that project out of the sealing member 113 as best shown in FIGS. 1B and 2.

The sealing member 113 comprises a sealing material which encapsulates the semiconductor chip 105, die pad 101 and external connection terminals 103 of the sensor semiconductor package 100. In this arrangement, the amount of air in the sensor semiconductor package 100 is minimized. In other examples, the sealing member may have an internal air-cavity. In these examples, the sealing member typically comprises a plastic-moulded body (open, and not sealed), and a lid which covers the plastic moulded body. The lid may be a ceramic or plastic lid, for example. The sealing material may be a plastic material and may, in particular, be a thermosetting resin. An example of a usable thermosetting resin is an epoxy resin.

The sensor semiconductor package 100 performs sensing functions and, beneficially, utilizes the exposed outer contact surface 117 of the die pad 101 as an electrode 117 for the sensor semiconductor package 100. Die pads are provided in existing semiconductor packages as heat sinks and are not electrically connected to the semiconductor chip. The present disclosure advantageously, utilizes the existing die pad of semiconductor packages as an electrode and electrically connects the die pad to the semiconductor chip such that the semiconductor chip may receive measurement signals from the electrode. In this way a self-contained semiconductor package 100 for performing sensing functions using an integral electrode is provided utilizing existing semiconductor package structures, and requiring minimal changes to existing, established, semiconductor package manufacturing techniques. Conventionally, a sensor semiconductor package is connected to a separate, standalone, electrode via a conductor extending from one or more of the external connection terminals.

The semiconductor chip 105 of the sensor semiconductor package 100 receives measurement signals from the electrode 117 and may perform one or more processing operations on the received measurements signals. The one or more processing operations may include signal processing operations which may comprise filtering, smoothing, or interpolation operations. The one or more processing operations may include feature extraction operations to extract one or more features from the (processed) measurement signals. The semiconductor chip 105 may comprise a controller. The controller may be a microcontroller. The controller may comprise a processor and a memory. The memory may store instructions which, when executed by the processor, cause the processor to perform one or more operations. The semiconductor chip 105 may comprise a data store for storing sensor data.

The semiconductor chip 105 is arranged to send and/or receive data via at least one of the external connection terminals 103. The at least one external connection terminal 103 is, in use, electrically connected a communication line to allow for data to be sent and/or received from the semiconductor chip 105. The communication line may be a bidirectional communication line to allow for data to be sent and received. At least one of the external connection terminals 103 functions as a ground for the semiconductor chip.

The semiconductor chip 105 may comprise additional circuitry for performing sensing functions. The semiconductor chip 105 may comprise circuitry for performing one or more of temperature sensing, humidity sensing, and motion sensing. In other words, the semiconductor chip 105 may comprise a temperature sensor, a humidity sensor, or a motion sensor. The motion sensor may comprise one or more of an accelerometer, gyroscope, and magnetometer. The motion sensor may comprise an inertial measurement unit.

Referring to FIGS. 5 to 8, there is shown another sensor semiconductor package 100' according to aspects of the present disclosure. The sensor semiconductor package 100' has a similar structure to the sensor semiconductor package 100 shown in FIGS. 1B to 4 and like reference numerals have been used to show like components. Importantly, the sensor semiconductor package 100' of FIGS. 5 to 8 comprises a plurality of die pads and in particular includes a first die pad 101 and a second die pad 101'. The semiconductor chip 105 is positioned such that it straddles the top surface of both the first die pad 101 and the second die pad 101'. The semiconductor chip 105 is electrically connected to the first die pad 101 by a first wire 109 and is electrically connected to the second die pad 101' by a second wire 109'.

The sealing member 113 exposes an outer contact surface 117 of the first die pad 101 and an outer contact surface 117' of the second die pad 101'. The outer contact surface 117 of the first die pad 101 forms a first electrode 117 of the sensor semiconductor package 100'. The outer contact surface 117'of the second die pad 101' forms a second electrode 117' of the sensor semiconductor package 100'. This arrangement therefore provides a sensor semiconductor package 100' with two integral electrodes 117, 117'. The two integral electrodes 117, 117' may form first and second electrodes 117, 117' of a bioelectrical sensor such an electrocardiography sensor. The two integral electrodes 117, 117' may for bipolar electrodes 117, 117' of an electromyography sensor and in particular a surface electromyography sensor.

Figure 9:
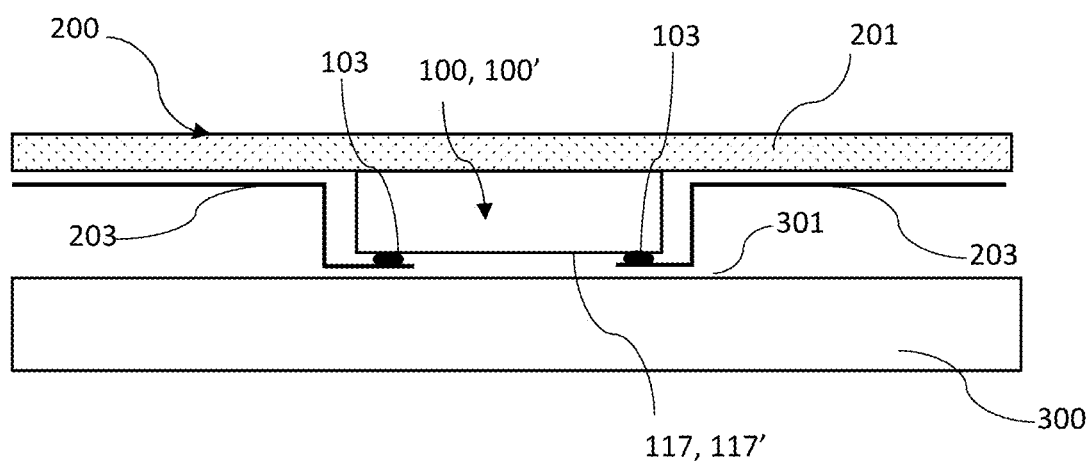
FIG. 9 is a cross-sectional view of an article according to aspects of the present disclosure positioned proximate to a skin surface of a user.

Referring to FIG. 9, there is shown an example article 200 comprising the sensor semiconductor package 100, 100' of FIGS. 1B to 8. The article 200 is a textile article 200 and comprises a textile material 201. The sensor semiconductor package 100, 100' is attached to the textile material 201. A top surface of the sensor semiconductor package 100, 100' is adhered to the textile material 201 using an adhesive. The bottom surface of the sensor semiconductor package 100, 100' faces away from the textile material 201 which means that the electrode(s) 117, 117' of the sensor semiconductor package 100, 100' face away from the textile material 201. This enables the electrode(s) 117, 117' to be positioned proximate to and optionally in contact with a skin surface 301 when the article 200 is worn by the user 300. Conductive traces 203 are also provided to electrically connect one or more of the external connection terminals 103 of the sensor semiconductor package 100, 100' to other electronic components.

Figure 10:
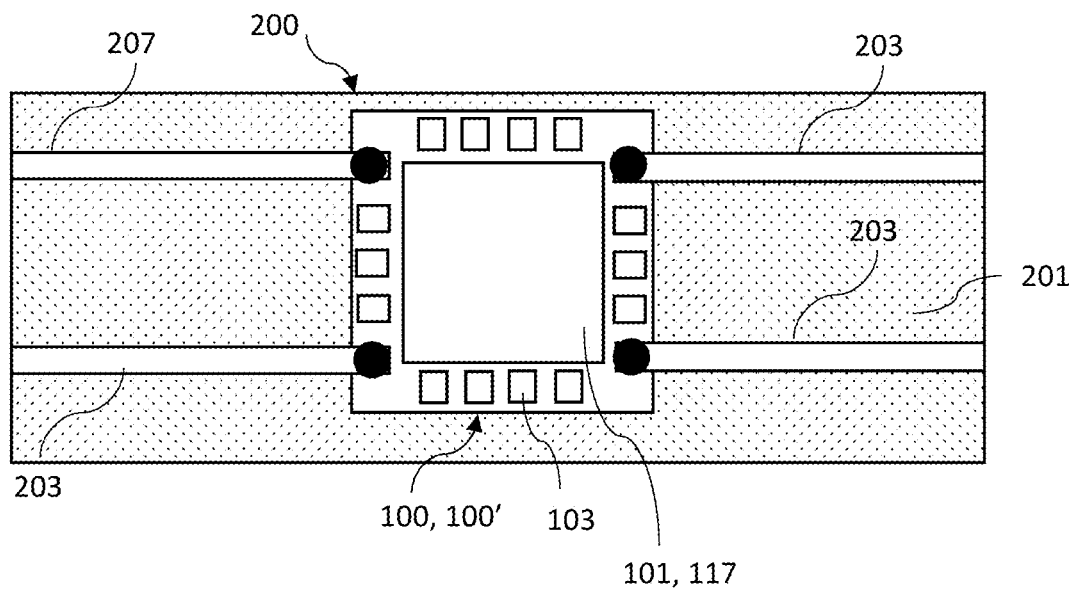
FIG. 10 is a bottom view of the article of FIG. 9.

Referring to FIG. 10, there is shown a view of the bottom surface of the article 200 of FIG. 9. FIG. 10 shows that in this example, there are four conductive traces 203 each connected to a different one of the external connection terminals 103. In this way, four of the external connection terminals 103 are able to be electrically connected to other, separate, electronic components. The remainder of the external connection terminals 103 are not electrically connected to the conductive traces 203. The external connection terminals 103 that are not electrically connected to the conductive traces 203 may be redundant or may not be electrically connected to the semiconductor chip. These external connection terminals 103 may still be beneficially provide additional mechanical advantage to the sensor semiconductor package 100 and may help the sensor semiconductor package 100 remain in attachment with the textile article 200.

Figure 11:
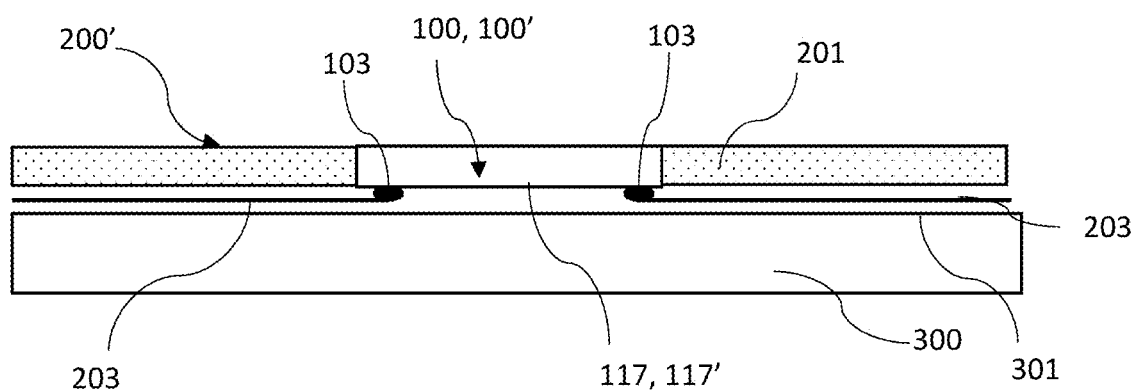
FIG. 11 is a cross-sectional view of another article according to aspects of the present disclosure positioned proximate to a skin surface of a user.

Referring to FIG. 11, there is shown another example article 200' comprising the sensor semiconductor package 100, 100' of FIGS. 1B to 8. In this example, the textile material 201 comprises an aperture through which the sensor semiconductor package 100, 100' is provided.

Figure 12:
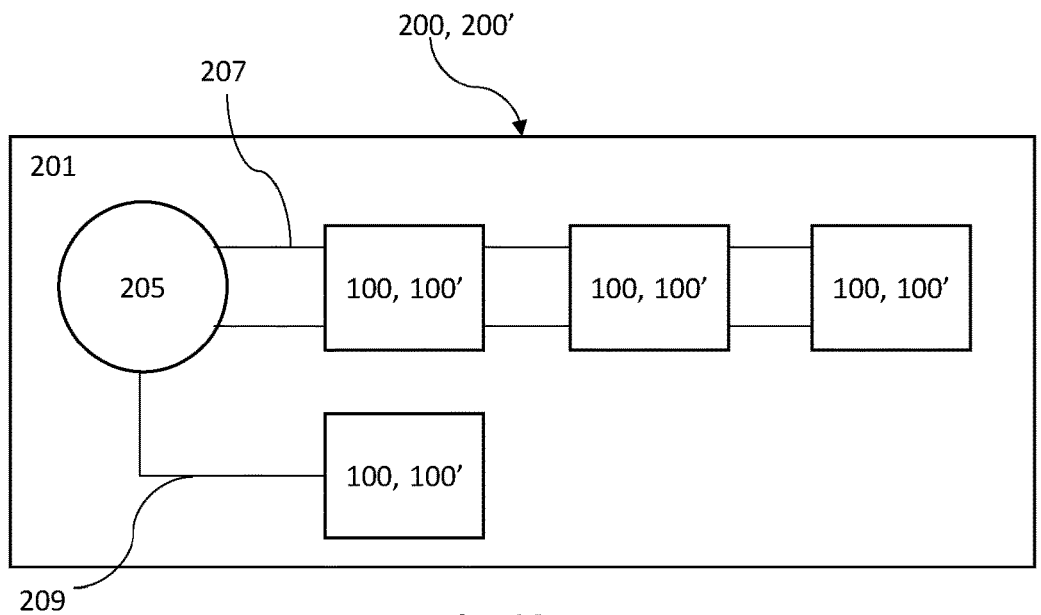
FIG. 12 is a schematic diagram of an example article according to aspects of the present disclosure.

Referring to FIG. 12, there is shown a schematic view of an example article 200, 200' according to aspects of the present disclosure. The article 200, 200' comprises a textile material 201. The article 200, 200' further comprises an electronics module 205 and a plurality (four in this example) of sensor semiconductor packages 100, 100'. Three of the sensor semiconductor packages 100, 100' are connected to the electronics module 205 via a shared communication bus 207. One of the sensor semiconductor packages 100, 100' is connected to the electronics module 205 via its own communication bus 209.

The electronics module 205 may be a removable electronics module 205 for the article 200, 200'. The electronics module 205 may be configured to be releasably mechanically coupled to the article 200, 200'. The mechanical coupling of the electronics module 205 to the article 200, 200' may be provided by a mechanical interface such as a clip, a plug and socket arrangement, etc. The mechanical coupling or mechanical interface may be configured to maintain the electronics module 205 in a particular orientation with respect to the article 200, 200' when the electronics module 200, 200' is coupled to the article 200, 200'. This may be beneficial in ensuring that the electronics module 205 is securely held in place with respect to the article 200, 200' and/or that any electronic coupling of the electronics module 205 and the article 200, 200' (or a component of the article 200, 200') can be optimized. The mechanical coupling may be maintained using friction or using a positively engaging mechanism, for example.

It may be desirable to avoid direct contact of the electronics module 205 with the wearer's skin while the article 200, 200' is being worn. In particular, it may be desirable to avoid the electronics module 205 coming into contact with sweat or moisture on the wearer's skin. The electronics module 205 may be provided with a waterproof coating or waterproof casing. For example, the electronics module 205 may be provided with a silicone casing. It may further be desirable to provide a pouch or pocket in the article 200, 200' to contain the electronics module 205 in order to prevent chafing or rubbing and thereby improve comfort for the wearer. The pouch or pocket may be provided with a waterproof lining in order to prevent the electronics module 205 from coming into contact with moisture.

The electronics module 205 may comprise a power source. The power source may comprise a plurality of power sources. The power source may be a battery. The battery may be a rechargeable battery. The battery may be a rechargeable battery adapted to be charged wirelessly such as by inductive charging. The power source may comprise an energy harvesting device. The energy harvesting device may be configured to generate electric power signals in response to kinetic events such as kinetic events performed by a wearer of the article 200, 200'. The kinetic event could include walking, running, exercising or respiration of the wearer. The energy harvesting material may comprise a piezoelectric material which generates electricity in response to mechanical deformation of the converter. The energy harvesting device may harvest energy from body heat of a wearer of the article 200, 200'. The energy harvesting device may be a thermoelectric energy harvesting device. The power source may be a super capacitor, or an energy cell.

The electronics module 205 may comprise a communicator. The communicator may be a mobile/cellular communicator operable to communicate the data wirelessly via one or more base stations. The communicator may provide wireless communication capabilities for the article 200, 200' and enables the article 200, 200' to communicate via one or more wireless communication protocols such as used for communication on: a wireless wide area network (WWAN), a wireless metroarea network (WMAN), a wireless local area network (WLAN), a wireless personal area network (WPAN), a near field communication (NFC), and a cellular communication network. The cellular communication network may be a fourth generation (4G) LTE, LTE Advanced (LTE-A), fifth generation (5G), sixth generation (6G), and/or any other present or future developed cellular wireless network. A first communicator of the electronics module 205 may be provided for cellular communication and a separate communicator may be provided for short-range local communication over WLAN, WPAN, NFC, or Bluetooth®, WiFi or any other electromagnetic RF communication protocol.

The electronics module 205 may comprise a Universal Integrated Circuit Card (UICC) that enables the wearable article to access services provided by a mobile network operator (MNO) or virtual mobile network operator (VMNO). The UICC may include at least a read-only memory (ROM) configured to store an V/MNO profile that the wearable article can utilize to register and interact with an V/MNO. The UICC may be in the form of a Subscriber Identity Module (SIM) card. The wearable article may have a receiving section arranged to receive the SIM card. In other examples, the UICC is embedded directly into a controller of the wearable article. That is, the UICC may be an electronic/embedded UICC (eUICC). A eUICC is beneficial as it removes the need to store a number of V/MNO profiles, i.e. electronic Subscriber Identity Modules (eSIMs). Moreover, eSIMs can be remotely provisioned. The article 200, 200' may comprise a secure element that represents an embedded Universal Integrated Circuit Card (eUICC).

Figure 13:
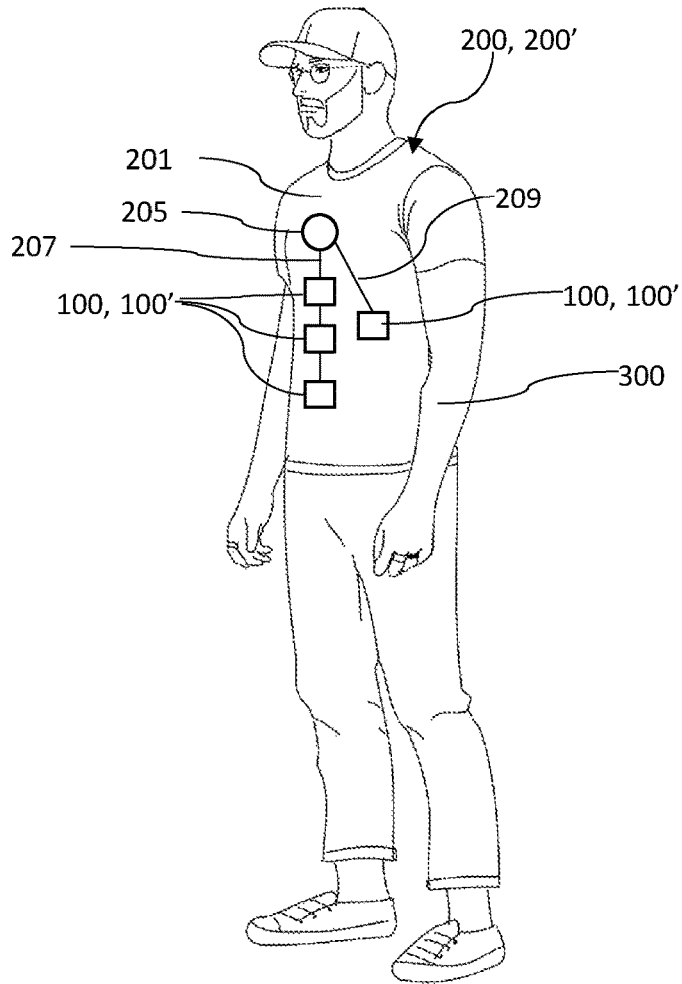
FIG. 13 is a simplified diagram showing a user wearing an article according to aspects of the present disclosure.

Referring to FIG. 13, there is shown an example article 200, 200' according to aspects of the present disclosure worn by a user 300. The article 200, 200' in this example is a garment and, in particular, comprises a textile material 201 which forms a T-shirt. The article 200, 200' further comprises an electronics module 205 and a plurality (four in this example) of sensor semiconductor packages 100, 100'. Three of the sensor semiconductor packages 100, 100' are connected to the electronics module 205 via a shared communication bus 207. One of the sensor semiconductor packages 100, 100' is connected to the electronics module 205 via its own communication bus 209. The sensor semiconductor packages 100, 100' are provided on the inside surface of the textile material 201 and are not visible externally. The sensor semiconductor packages 100, 100' are positioned such that their electrodes are able to contact the skin.

Figure 14:
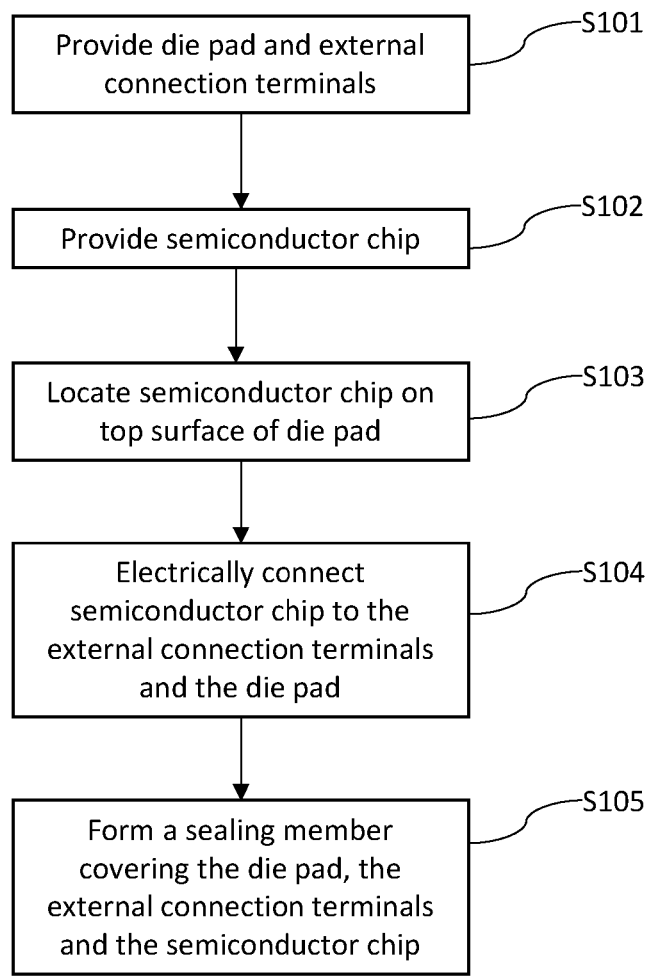
FIG. 14 is a flow diagram of an example method of manufacturing a sensor semiconductor package according to aspects of the present disclosure.

Referring to FIG. 14, there is shown a process flow diagram for an example method according to aspects of the present disclosure of manufacturing a sensor semiconductor package.

Step S101 of the method comprises providing at least one die pad and a plurality of external connection terminals. Step S102 of the method comprises providing a semiconductor chip. Step S103 of the method comprises locating the semiconductor chip on a top surface of the at least one die pad. Step S104 of the method comprises electrically connecting the semiconductor chip to the plurality of external connection terminals and the at least one die pad. Step S105 of the method comprises forming a sealing member covering the die pad, the plurality of external connection terminals and the semiconductor surface and exposing an outer terminal of each of the plurality of external connection terminals and an outer contact surface of the at least one die pad, wherein the outer contact surface of the at least one die pad forms an electrode of the sensor semiconductor package.

Providing the at least one die pad and a plurality of external connection terminals may comprise providing a lead frame including the at least one die pad and the plurality of external connection terminals. In some examples, the lead frame comprises a plurality of regions to be separated from one another to provide a plurality of sensor semiconductor packages. Each of the plurality of region comprises at least one die pad and a plurality of external connection terminals. For each of the regions, a semiconductor chip is located on a top surface of the at least one die pad, and the semiconductor chip is electrically connected to the plurality of external connection terminals and the at least one die pad. For each of the regions, a sealing member is then formed covering the die pad, the plurality of external connection terminals and the semiconductor surface and exposing an outer terminal of each of the plurality of external connection terminals and an outer contact surface of the at least one die pad, wherein the outer contact surface of the at least one die pad forms an electrode of the sensor semiconductor package. The plurality of regions may then be separated from one another to form the plurality of semiconductor packages.

The sensor semiconductor package according to aspects of the present disclosure is therefore manufactured using existing, established, semiconductor package manufacturing techniques. The additional step of electrically connecting the die pad to the semiconductor chip does not overly complicate the semiconductor package manufacturing process compared to conventional arrangements as this step can be performed using existing techniques already used for connecting the semiconductor chip to the external connection terminals (e.g. wire bonding). The manufacturing techniques enables many sensor semiconductor packages to be manufactured at the same time. Therefore, aspects of the present disclosure facilitate the rapid, and low cost, manufacture of sensor semiconductor packages.

Figure 15:
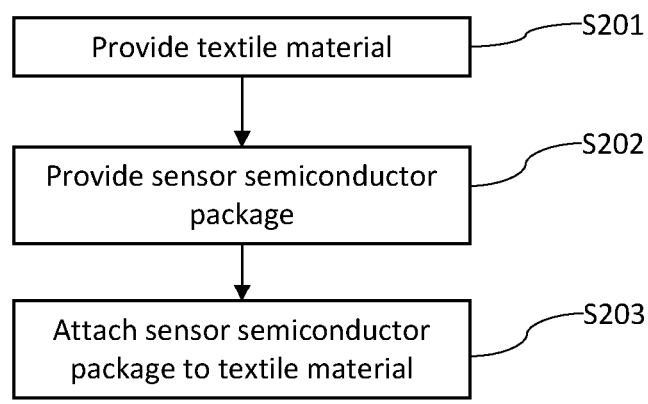
FIG. 15 is a flow diagram of an example method of manufacturing an article according to aspects of the present disclosure.

Referring to FIG. 15, there is shown a process flow diagram for an example method according to aspects of the present disclosure of manufacturing an article. Step S201 of the method comprises providing a textile material. Step S202 of the method comprises providing a sensor semiconductor package. Step S203 of the method comprises attaching the sensor semiconductor package to the textile material.

Figure 16:
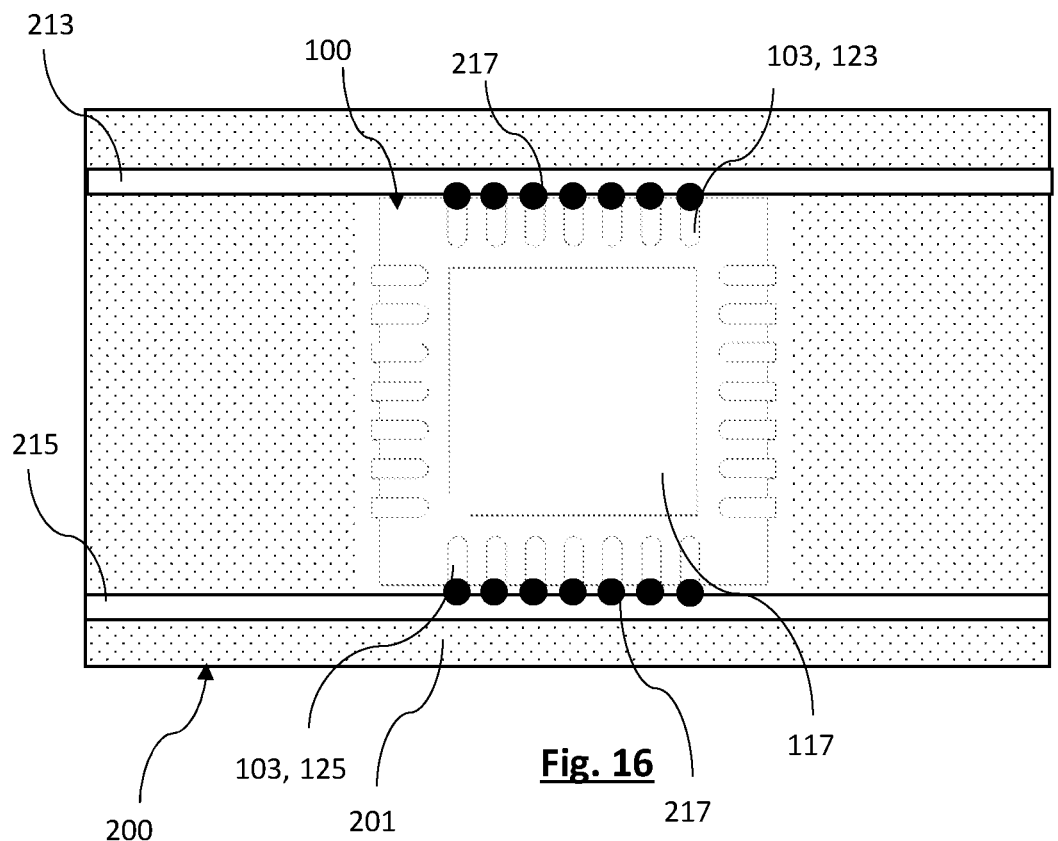
FIG. 16 is a bottom view of an article according to aspects of the present disclosure.

Referring to FIG. 16, there is shown a view of the bottom surface of an article 200 according to aspects of the present disclosure. The article 200 comprises the sensor semiconductor package 100 of FIGS. 1B to 4. Additionally, or separately, the article 200 may comprise the sensor semiconductor package 100' of FIGS. 5 to 8. The article 200 is a textile article 200 and comprises a textile material 201. The sensor semiconductor package 100 is attached to the textile material 201. A top surface of the sensor semiconductor package 100 is adhered to the textile material 201 using an adhesive. The bottom surface of the sensor semiconductor package 100 faces away from the textile material 201 which means that the electrode 117 of the sensor semiconductor package 100 faces away from the textile material 201. This enables the electrode 117 to be positioned proximate to and optionally in contact with a skin surface when the article 200 is worn by a user. The textile material 201 comprises a first electrically conductive yarn 213 and a second electrically conductive yarn 215 that extend along at least part of the length of the textile material 201. The first and second electrically conductive yarns 213, 215 extend parallel to one another and are spaced apart such that the sensor semiconductor package 100 is located between the first and second electrically conductive yarns 213, 215. The first and second electrically conductive yarns 213, 215 are incorporated into the textile material 201 using a twin-needle stitch. One or a plurality of first external connection terminals 103, 123 (seven are shown in FIG. 16) located along a first side of the sensor semiconductor package 100 are electrically connected to the first electrically conductive yarn 213. One or a plurality of second external connection terminals 103, 125 (seven are shown in FIG. 16) located along a second side of the sensor semiconductor page 100, opposite to the first side, are electrically connected to the second electrically conductive yarn 215. The first and second plurality of external connection terminals 103, 125 are soldered 217 to the first and second conductive yarns 213, 215. The remainder of the external connection terminals 103 are not electrically connected to the conductive traces 213, 215. The external connection terminals 103 that are not electrically connected to the conductive traces 213, 215 may be redundant or may not be electrically connected to the semiconductor chip. These external connection terminals 103 may still be beneficially provide additional mechanical advantage to the sensor semiconductor package 100 and may help the sensor semiconductor package 100 remain in attachment with the textile article 200.

Figure 17:
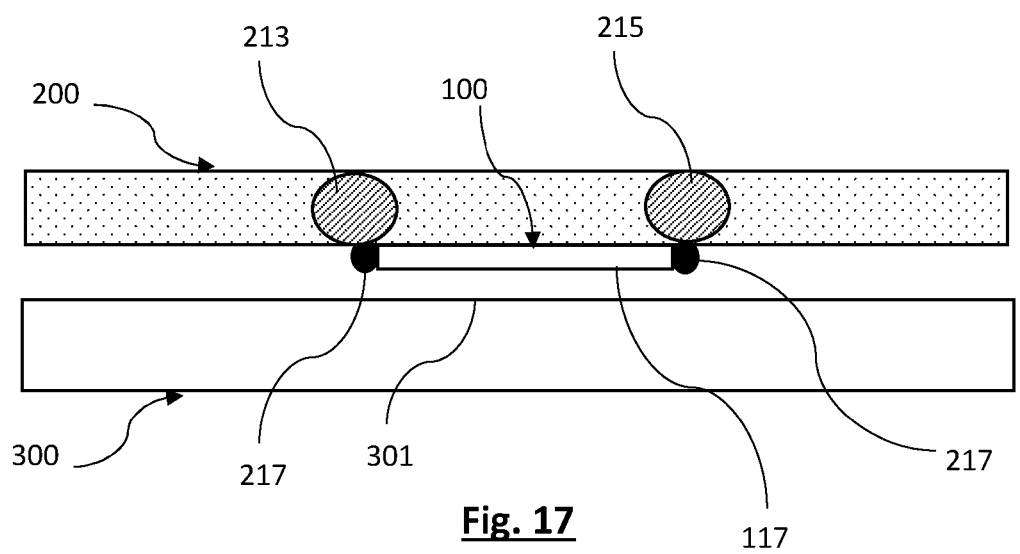
FIG. 17 is a cross-sectional view of the article of FIG. 16 positioned proximate to a skin surface of a user.

Referring to FIG. 17, there is shown a side view of the article 200 of FIG. 16. The article 200 is positioned proximate to a skin surface 301 of a user 300. The electrode 117 of the sensor semiconductor package 200 faces the skin surface 301.

Figure 18:
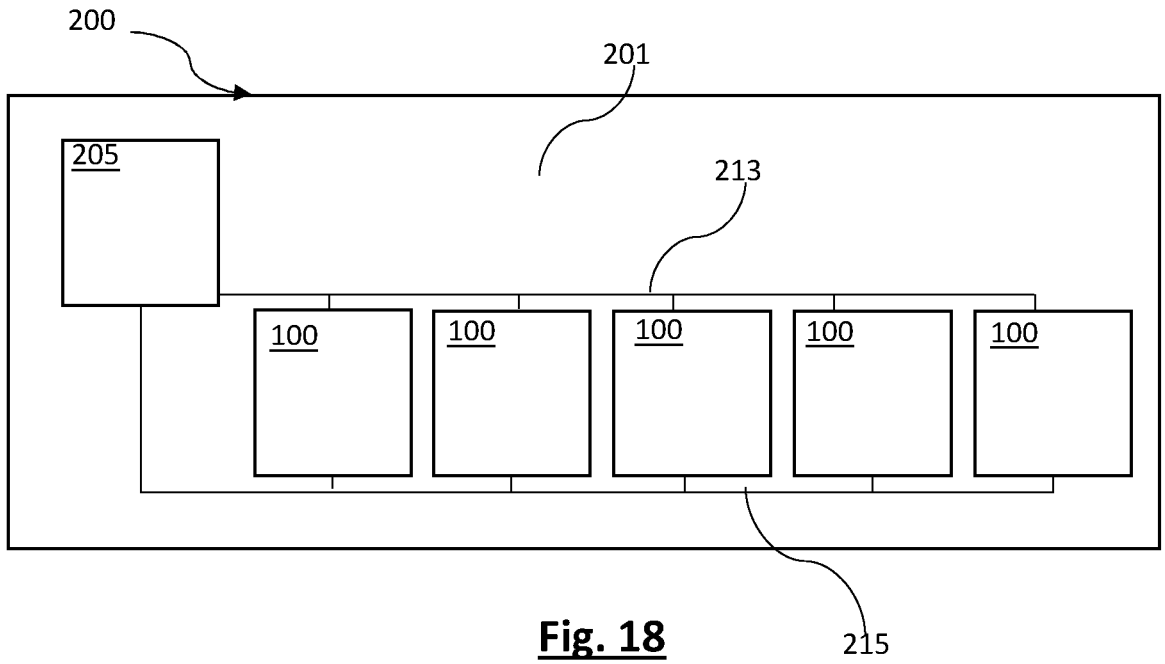
FIG. 18 is a schematic diagram of an example article according to aspects of the present disclosure.

Referring to FIG. 18, there is shown a schematic view of an example article 200 according to aspects of the present disclosure. The article 200 comprises a textile material 201. The article 200 further comprises an electronics module 205 and a plurality (five in this example) of sensor semiconductor packages 100. Additionally, or separately, the article 200 may comprise the sensor semiconductor package 100' of FIGS. 5 to 8. The five sensor semiconductor packages 100 are all electrically connected to the first electrically conductive yarn 213 and the second electrically conductive yarn 215 in the manner described above in relation to FIGS. 16 and 17.

The first electrically conductive yarn 213 is a bidirectional line for the article 200 which enables data to be transferred between the electronics module 205 and the sensor semiconductor packages 100. The bidirectional line 213 is a single-wire bidirectional line, and the semiconductor chip of the sensor semiconductor packages 100 send and/or receive data over the singe-wire bidirectional line using a single-wire communication protocol. The second electrically conductive yarn 215 is a return line for the article 200. The semiconductor chips of the semiconductor packages 100 are connected to ground by the return line.

This arrangement enables a plurality of sensor semiconductor packages 100 to be connected to an electronics module 205 using a single wire bidirectional line 213. This is the minimum possible number of conductive lines that may be provided. This reduces the number of physical hardware connections required for data transmission to/from the sensor semiconductor packages 100 and is particularly beneficial for wearable article implementations. It is appreciated that even with a single-wire protocol, a separate ground/return line 215 is still provided. This single-wire arrangement is particularly beneficial as it allows a number of sensor semiconductor packages 100 to be communicatively connected to one another and an electronics module 205 via a single conductive yarn 213 stitched into the textile material. This simplifies the design, cost, and manufacture of the article 200 as fewer conductive yarns are required to be incorporated into the textile article 201. The present disclosure is, however, not limited to single-wire bidirectional lines although particular advantages are achieved in these examples. Two-wire bidirectional lines, three-wire bidirectional lines or four or more wire bidirectional lines may also be used in some examples. The bidirectional lines may use any existing serial protocol such as Serial Peripheral Interface (SPI), Inter-Integrated Circuit (I2C), Controller Area Network (CAN), Recommended Standard 232 (RS-232), and 1-wire.

Figure 19:
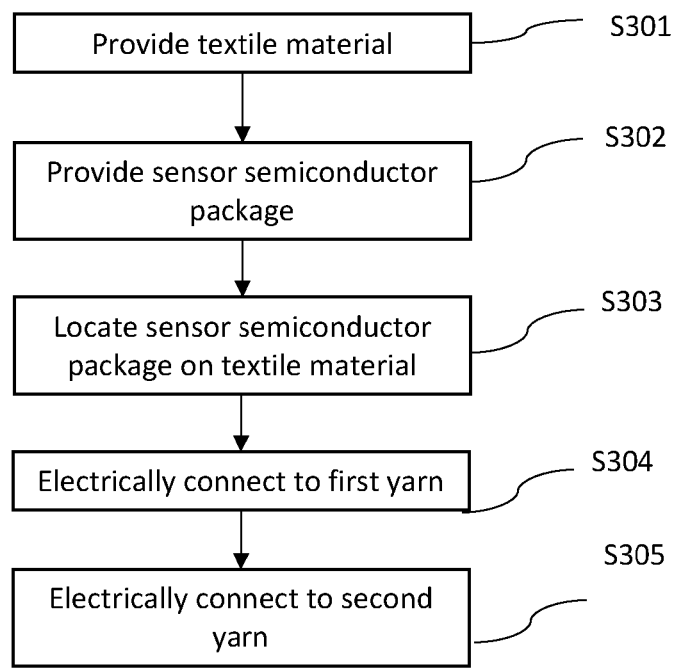
FIG. 19 is a flow diagram of an example method of manufacturing an article according to aspects of the present disclosure.

Referring to FIG. 19, there is shown a process flow diagram for an example method according to aspects of the present disclosure of manufacturing an article.

Step S301 of the method comprises providing a textile material. the textile material comprising a first electrically conductive yarn and a second electrically conductive yarn, the first electrically conductive yarn and the second electrically conductive yarn extending along at least part of the length of the textile material.

Step S302 of the method comprises providing a sensor semiconductor package. The sensor semiconductor package comprises: a first external connection terminal; a second external connection terminal; a semiconductor chip electrically connected to the first external connection terminal and the second external connection terminal; and a sealing member covering the first and second external connection terminals and the semiconductor chip and exposing an outer terminal of each of the first and second external connection terminals.

Step S303 of the method comprises locating the sensor semiconductor package on the textile material. Step S304 of the method comprises electrically connecting the first electrically conductive yarn is to the first external connection terminal. Step S305 of the method comprises electrically connecting the second electrically conductive yarn to the second external connection terminal.

Figure 20:
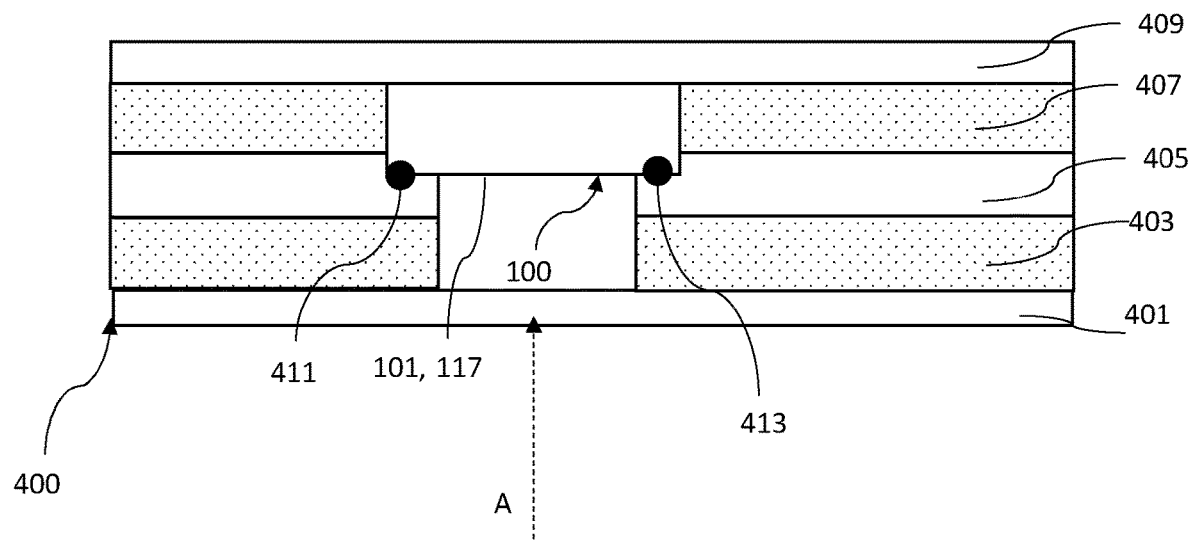
FIG. 20 is a cross-sectional view of a layer structure according to aspects of the present disclosure.

Referring to FIG. 20, there is shown a cross-sectional view of a layer structure 400 according to aspects of the present disclosure. The layer structure 400 comprises a first insulating layer 403 and a second insulating layer 407. An electrically conductive layer 405 is positioned between the first insulating layer 403 and the second insulating layer 407. A sensor semiconductor package 100 is provided on the electrically conductive layer 405. The sensor semiconductor package 100 is the package 100 of FIGS. 1B to 4. Additionally or separately, the layer structure 400 may comprise the sensor semiconductor package of FIGS. 5 to 8. A first external connection terminal of the sensor semiconductor package 100 is electrically connected to the electrically conductive layer 403 at connection point 411. A second external connection terminal is electrically connected to the electrically conductive layer 403 at connection point 413. The layer structure 400 additionally comprises a transfer layer 401 onto which the first insulating layer 403 is provided.

The first insulating layer 403 and the electrically conductive layer 405 include an opening which exposes the electrode 117 of the sensor semiconductor package 100. This means that the electrode 117 is not covered by the electrically conductive layer 405 or the first insulating layer 403.

The first insulating layer 403 is a non-conductive ink layer 403 comprising a non-conductive ink. The second insulating layer 407 is a non-conductive ink layer 407 comprising a non-conductive ink. The non-conductive ink layer may be any suitable printing ink which is non-conductive. The electrically conductive layer 405 comprises an electrically conductive ink. The electrically conductive ink may be any suitable electrically conductive ink.

The layer structure 400 further comprises a transfer layer 401. The first insulating layer 403 is provided on the transfer layer 401. The transfer layer 401 is not required to have an opening to expose the electrode 117 because the transfer layer 401 is removed once the layer structure 400 is attached to an article. The transfer layer 401 may be any suitable layer onto which ink may be printed. The transfer layer 401 may be a polyester film or paper film for example.

The layer structure 400 further comprises an adhesive layer 409. The adhesive layer 409 covers the second insulating layer 407 and the sensor semiconductor package 100. Adhesive layer 409 is used to adhere the layer structure 400 to a surface. The adhesive layer 409 may comprise a water based adhesive, a solvent based adhesive, a printable adhesive, a powder adhesive or any other suitable adhesive which is capable of the layer structure 400 to a surface. The adhesive layer 409 may be a printable adhesive In the example of FIG. 20, the second insulating layer 407 does not cover the sensor semiconductor package 100. This is not required in all embodiments. The sensor semiconductor package 100 may cover second insulating layer 407. Moreover, the layer structure 400 is not limited to the number of layers shown in FIG. 20 and additional layers may utilized to provide increased functionality. That is, the first insulating layer 403 may not be in direct contact with electrically conductive layer 405. Similarly, the second insulating layer 407 may not be in direct contact with electrically conductive layer 405.

Figure 21:
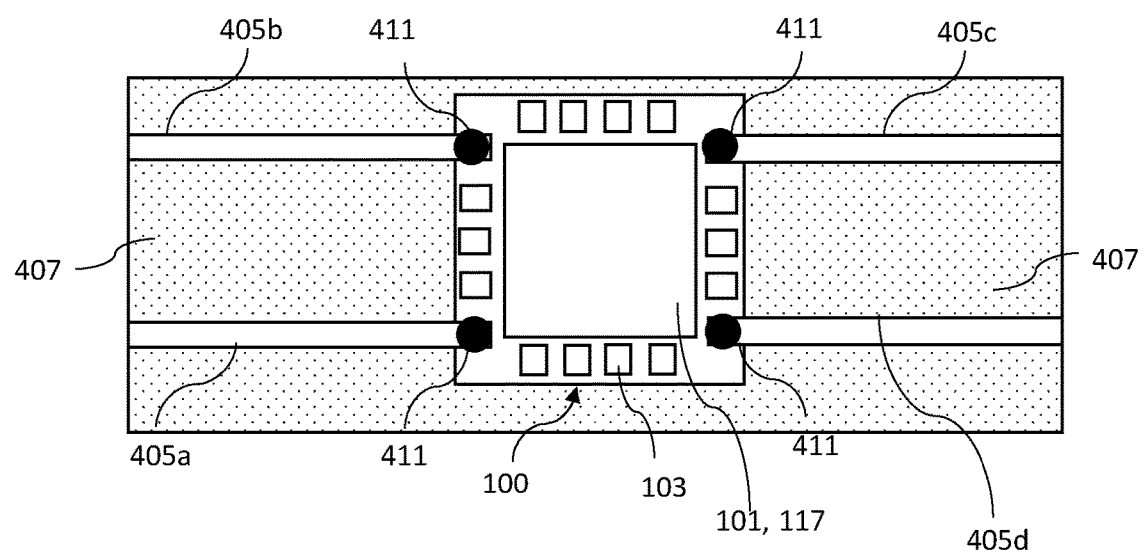
FIG. 21 is a bottom view of the layer structure of FIG. 20.

Referring to FIG. 21, there is shown a view of the layer structure of FIG. 20 in the direction of arrow "A". In this view, the transfer layer 401 and the first insulating layer 403 are not shown so as to improve the visibility of the conductive layer 405. The conductive layer 405 comprises four separate conductive traces 405a-405d. The four conductive traces 405a-405d are each connected to a different one of the external connection terminals 103 via connection points 411. In this way, four of the external connection terminals 103 are able to be electrically connected to other, separate, electronic components. The remainder of the external connection terminals 103 are not electrically connected to the conductive traces 405a-405d in this example. The external connection terminals 103 that are not electrically connected to the conductive traces 405a-405d may be redundant or may not be electrically connected to the semiconductor chip. These external connection terminals 103 may still be beneficially provide additional mechanical advantage to the sensor semiconductor package 100 and may help the sensor semiconductor package 100 remain in attachment with the rest of the layer structure.

Referring to FIG. 11 there is shown a cross-sectional view of an article 200 according to aspects of the present disclosure. The article 200 comprises a textile material 201 and a layer structure 400 as shown in FIGS. 20 and 21. The adhesive layer 409 of the layer structure 400 is attached to a surface of the textile material 201. The transfer layer is not present and has been removed to expose the electrode 117 of the sensor semiconductor package 100. In this way, the electrode 117 is able to approach or contact a skin surface of a user such as when the article 200 is worn.

Figure 22:
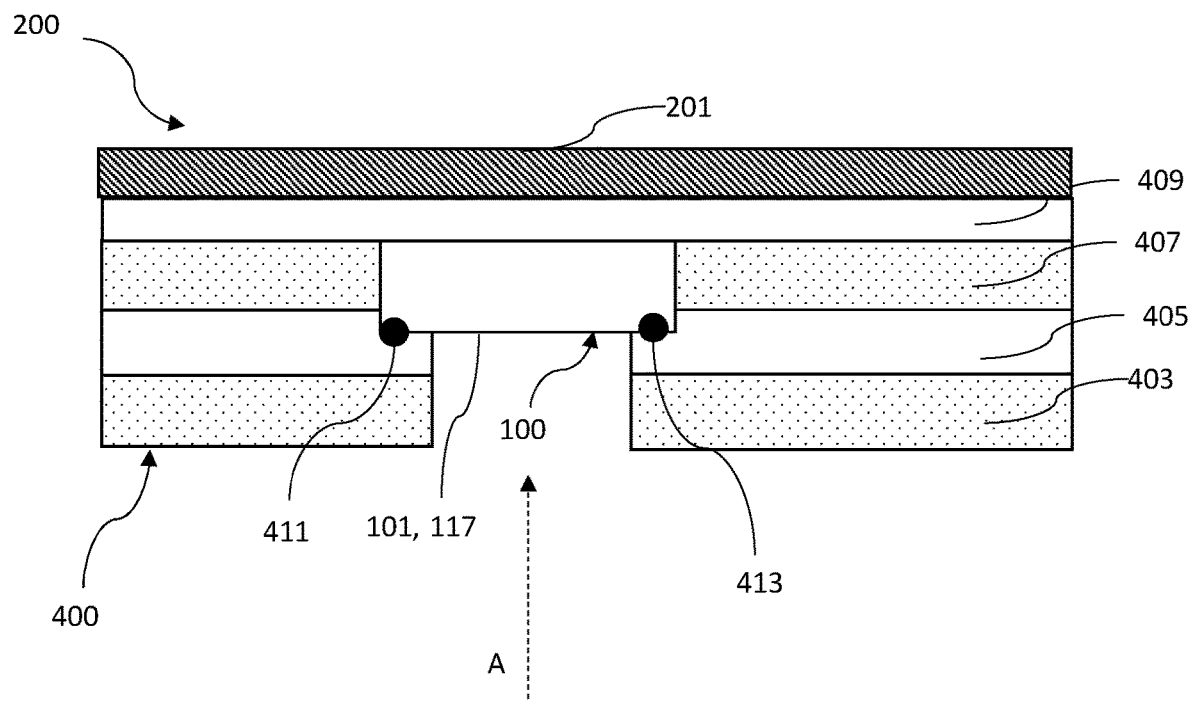
FIG. 22 is a cross-sectional view of an example article according to aspects of the present disclosure.

It will be appreciated that the relative thickness of the layers shown in FIGS. 20 to 22 is just for illustration purposes and may not reflect the actual thickness of the layers in the layer structure. Moreover, the thickness of the layer can be adapted by the skilled person based on factors such as the type of ink used and the number of printing operations performed.

Figure 23:
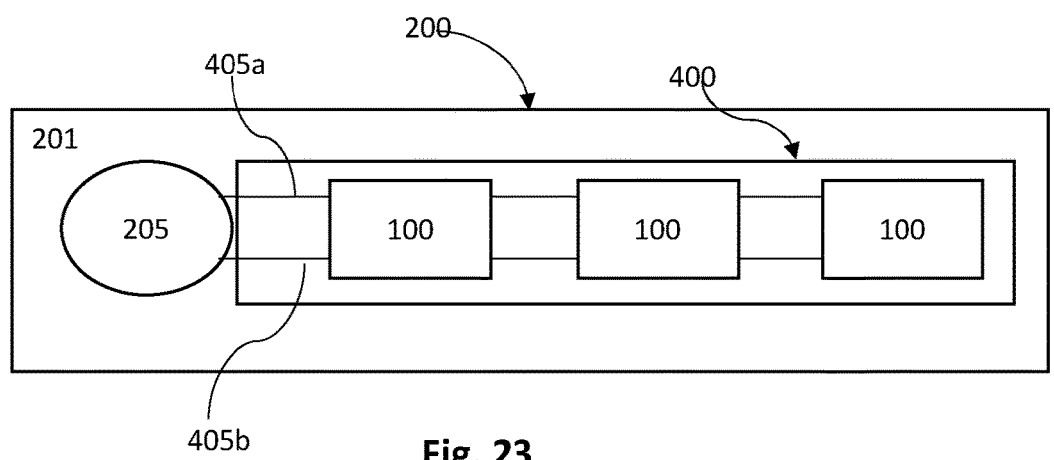
FIG. 23 is a schematic diagram of an example article according to aspects of the present disclosure.

Referring to FIG. 23, there is shown a schematic view of an example article 200 according to aspects of the present disclosure. The article 200 comprises a textile material 201. The article 200 further comprises an electronics module 205 and a layer structure 400 according to the present disclosure attached to the textile material 201. The article 200 comprises a plurality (three in this example) of sensor semiconductor packages 100. Additionally, or separately, the article 200 may comprise the sensor semiconductor package 100' of FIGS. 5 to 8. The three sensor semiconductor packages 100 are all electrically connected to the electrically conductive layer of the layer structure 400.

The layer structure 400 in FIG. 23 comprises a first conductive trace 405a and a second conductive trace 405b. A first external connection terminal of each of the sensor semiconductor packages 100 is connected to the first conducive trace 405a. A second external connection terminal of each of the sensor semiconductor packages 100 is connected to the second conductive trace 405b. The layer structure 400 comprises one or more openings in the first or second insulating layers to enable the electronics module 205 to electrically connect to the electrically conductive layer and thus electrically connect to the sensor semiconductor packages 100. The electronics module 205 may have one or more conductive elements such as studs, pads or prongs to extend through the openings to contact the electrically conductive layer. Of course, other mechanisms for connecting an electronics module 205 to an electrically conductive layer are within the scope of the present disclosure.

The first conductive trace 405a is a bidirectional line for the article 200 which enables data to be transferred between the electronics module 205 and the sensor semiconductor packages 100. The bidirectional line 405a is a single-wire bidirectional line, and the semiconductor chip of the sensor semiconductor packages 100 send and/or receive data over the singe-wire bidirectional line using a single-wire communication protocol. The second conductive trace 405b is a return line for the article 200. The semiconductor chips of the semiconductor packages 100 are connected to ground by the return line.

This arrangement enables a plurality of sensor semiconductor packages 100 to be connected to an electronics module 205 using a single wire bidirectional line 405a. This is the minimum possible number of conductive lines that may be provided. This reduces the number of physical hardware connections required for data transmission to/from the sensor semiconductor packages 100 and is particularly beneficial for wearable article implementations. It is appreciated that even with a single-wire protocol, a separate ground/return line 405b is still provided. This single-wire arrangement is particularly beneficial as it allows a number of sensor semiconductor packages 100 to be communicatively connected to one another and an electronics module 205 via a single conductive trace 405a in the layer structure. This simplifies the design, cost, and manufacture of the layer structure 400. The present disclosure is, however, not limited to single-wire bidirectional lines although particular advantages are achieved in these examples. Two-wire bidirectional lines, three-wire bidirectional lines or four or more wire bidirectional lines may also be used in some examples. The bidirectional lines may use any existing serial protocol such as Serial Peripheral Interface (SPI), Inter-Integrated Circuit (I2C), Controller Area Network (CAN), Recommended Standard 232 (RS-232), and 1-wire.

Figure 24:
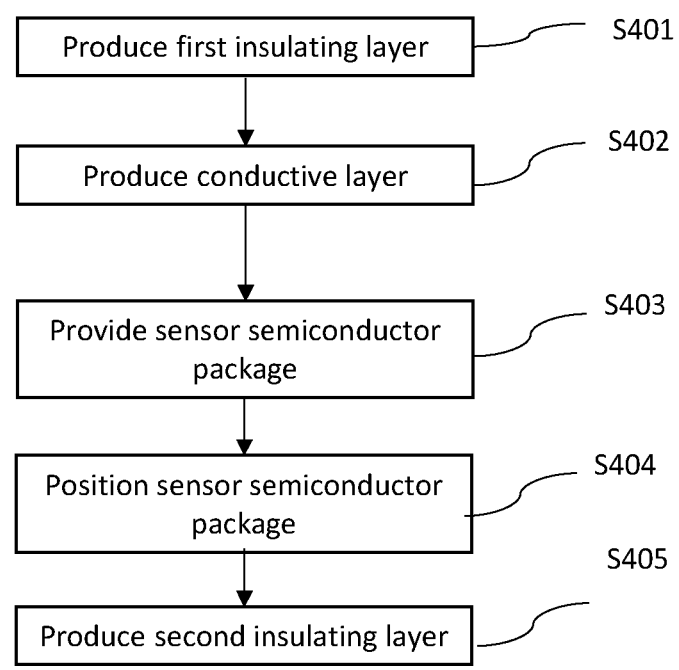
FIG. 24 is a flow diagram of an example method of manufacturing a sensor layer structure according to aspects of the present disclosure.

Referring to FIG. 24, there is shown a process flow diagram for an example method according to aspects of the present disclosure of manufacturing a layer structure. The method uses a transfer printing process to form the layer structure. The transfer printing process may be a screen printing process, reel-to-reel printing, dot matrix printing, laser printing, cylinder press printing, ink jet printing, flexographic printing, lithographic printing, offset printing, digital printing, gravure printing or xerographic printing, or other known printing process.

Step S401 of the method comprises printing non-conductive ink onto a transfer layer to produce a first insulating layer.

Step S402 of the method comprises printing an electrically conductive ink onto said first non-conductive printed ink layer to produce an electrically conductive layer.

Step S403 of the method comprises providing a sensor semiconductor package according to the present disclosure such as the sensor semiconductor package of any of FIGS. 1B to 8.

Step S404 of the method comprises positioning the sensor semiconductor package on the electrically conductive layer such that the electrically conductive layer is electrically connected to the first and second external connection terminals.

Step S405 of the method comprises printing non-conductive ink over said electrically conductive layer to produce a second insulating layer.

The first insulating layer may be cured prior to the step of printing the electrically conductive layer. The electrically conductive layer may be cured prior to the steps of positioning the sensor semiconductor package on the electrically conductive layer and printing the second insulating layer. In some examples, however, the sensor semiconductor package is positioned on the electrically conductive layer before the electrically conductive layer is cured. Curing may involve drying the layer.

Following the production of the second insulating layer, the method may further comprise applying an adhesive over the second insulating layer to produce an adhesive layer. The adhesive layer may be printed or otherwise applied to the second insulating layer. The adhesive layer may be applied before or after the second insulating layer is cured depending on factors such as the type of adhesive used.

In an example method of manufacturing an article, a layer structure as manufactured in the method of FIG. 25 is attached to a surface of the article using the adhesive layer. The transfer layer is then removed.

In some examples of the present disclosure, the sensor semiconductor package has a QFN-type structure (Quad Flat Non-lead Package). The present disclosure is not limited to QFN-type structures and could, for example, be any type of surface-mount package. Other example packages include Quad Flat Packages (QFP), and Ball Grid Array (BGA) packages.

The sensor semiconductor package is not limited to only one semiconductor chip and may include at least one semiconductor chip. In some examples, the sensor semiconductor package comprises a plurality of semiconductor chips. Each of the plurality of semiconductor chips may be electrically connected to a different die pad of the sensor semiconductor package.

The sensor semiconductor package may be used for sensing any kind of signal which requires the use of an electrode. In preferred examples, the sensor semiconductor package is biosensor (biosignal sensor) semiconductor package and the electrode(s) of the biosensor semiconductor package are for monitoring a biosignal of a living body. The biosignal may be a bioelectrical signal or a bioimpedance signal for example. Particular examples include the biosensor semiconductor package being an electrocardiography (ECG) semiconductor sensor package and/or an electromyography semiconductor (EMG) semiconductor sensor package.

The sensor semiconductor package in accordance with the present disclosure may have any size as appropriately selected by the skilled person in the art. The sensor semiconductor package may have a width of less than or equal to 50 mm, preferably less than or equal to 20 mm, preferably less than or equal to 10 mm, preferably less than or equal to 6 mm. The sensor semiconductor package may have a length of less than or equal to 50 mm, preferably less than or equal to 20 mm, preferably less than or equal to 10 mm, preferably less than or equal to 6 mm. The sensor semiconductor package may have a width of greater than or equal to 3 mm, preferably greater than or equal to 4 mm. The sensor semiconductor package may have a width×length of between 3 mm×3 mm and 50 mm×50 mm, preferably between 4 mm×4 mm and 10 mm×10 mm, preferably still between 4 mm×4 mm and 6 mm×6 mm. The size of the sensor semiconductor package may depend on factors such as the number of external connection terminals and the size of the semiconductor chip. Generally, a sensor semiconductor package having 24 external connection terminals will have a width×length of 4 mm×4 mm.

At least some of the example embodiments described herein may be constructed, partially or wholly, using dedicated special-purpose hardware. Terms such as 'component', 'module' or 'unit' used herein may include, but are not limited to, a hardware device, such as circuitry in the form of discrete or integrated components, a Field Programmable Gate Array (FPGA) or Application Specific Integrated Circuit (ASIC), which performs certain tasks or provides the associated functionality. In some embodiments, the described elements may be configured to reside on a tangible, persistent, addressable storage medium and may be configured to execute on one or more processors. These functional elements may in some embodiments include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Although the example embodiments have been described with reference to the components, modules and units discussed herein, such functional elements may be combined into fewer elements or separated into additional elements. Various combinations of optional features have been described herein, and it will be appreciated that described features may be combined in any suitable combination. In particular, the features of any one example embodiment may be combined with features of any other embodiment, as appropriate, except where such combinations are mutually exclusive. Throughout this specification, the term "comprising" or "comprises" means including the component(s) specified but not to the exclusion of the presence of others.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A sensor semiconductor package, comprising:
   at least one die pad;
   a plurality of external connection terminals;
   a semiconductor chip located on a top surface of the at least one die pad and electrically connected with the plurality of external connection terminals and the at least one die pad, wherein at least one wire extends from the semiconductor chip to electrically connect the semiconductor chip to the at least one die pad, and wherein a plurality of wires extend from the semiconductor chip to electrically connect the semiconductor chip to the plurality of external connection terminals; and
   a sealing member covering the at least one die pad, the plurality of external connection terminals and the semiconductor chip and exposing an outer terminal of each of the plurality of external connection terminals and an outer contact surface of the at least one die pad, wherein the outer contact surface of the at least one die pad forms an electrode of the sensor semiconductor package,
   wherein the semiconductor chip is arranged to receive a measurement signal from the at least one die pad.

2. A sensor semiconductor package according to claim 1, wherein the semiconductor chip is arranged to perform at least one processing operation on the received measurement signal.

3. A sensor semiconductor package according to claim 1, wherein the semiconductor chip is arranged to send and receive data via at least one of the plurality of external connection terminals.

4. A sensor semiconductor package according to claim 1, wherein at least one of the plurality of external connection terminals functions as a ground for the semiconductor chip.

5. A sensor semiconductor package according to claim 1, wherein the at least one die pad comprises a first die pad and a second die pad, wherein the semiconductor chip is electrically connected to the first die pad and the second die pad, and wherein the sealing member exposes an outer contact surface of the first die pad and an outer contact surface of the second die pad, and wherein the outer contact surface of the first die pad forms a first electrode of the sensor semiconductor package, and wherein the outer contact surface of the second die pad forms a second electrode of the sensor semiconductor package.

6. A sensor semiconductor package according to claim 1, wherein the sensor semiconductor package is a biosensor semiconductor package, and wherein the electrode of the biosensor semiconductor package is for monitoring a biosignal of a living body.

7. A sensor semiconductor package as claimed in claim 6, wherein the electrode of the biosensor semiconductor package is for monitoring a bioelectrical signal of the living body, wherein the electrode of the biosensor semiconductor package is for monitoring a biopotential signal of the living body and wherein the electrode of the biosensor semiconductor package is for monitoring a bioimpedance signal of the living body.

8. A sensor semiconductor package according to claim 6, wherein the biosensor semiconductor package is an electrocardiography semiconductor sensor package, and wherein the biosensor semiconductor package is an electromyography semiconductor sensor package.

9. An article comprising the sensor semiconductor package according to claim 1.

10. An article as claimed in claim 9, wherein the article is a wearable article.

11. An article as claimed in claim 10, wherein the wearable article is a garment.

12. A method for manufacturing an article, the method comprising:
providing a textile material;
providing a sensor semiconductor package according to claim 1; and
attaching the sensor semiconductor package to the textile material.

13. A sensor semiconductor package according to claim 7, wherein the biosensor semiconductor package is an electrocardiography semiconductor sensor package, and/or wherein the biosensor semiconductor package is an electromyography semiconductor sensor package.

14. A sensor semiconductor package as claimed in claim 6, wherein the electrode of the biosensor semiconductor package is for monitoring a bioelectrical signal of the living body, and wherein the electrode of the biosensor semiconductor package is for monitoring a biopotential signal of the living body.

15. A sensor semiconductor package as claimed in claim 6, wherein the electrode of the biosensor semiconductor package is for monitoring a bioelectrical signal of the living body, and wherein the electrode of the biosensor semiconductor package is for monitoring a bioimpedance signal of the living.

16. A sensor semiconductor package according to claim 6, wherein the biosensor semiconductor package is an electrocardiography semiconductor sensor package.

17. A sensor semiconductor package according to claim 6, wherein the biosensor semiconductor package is an electromyography semiconductor sensor package.

18. A sensor semiconductor package according to claim 1, wherein the semiconductor chip is arranged to send or receive data via at least one of the plurality of external connection terminals.

* * * * *

UNITED STATES PATENT AND TRADEMARK OFFICE
CERTIFICATE OF CORRECTION

PATENT NO. : 12,288,736 B2  
APPLICATION NO. : 17/772242  
DATED : April 29, 2025  
INVENTOR(S) : Michael John Lynch Page 1 of 1

It is certified that error appears in the above-identified patent and that said Letters Patent is hereby corrected as shown below:

On the Title Page

Item (54), and in the Specification, Column 1 Line 1 The title - Please insert --SEMICONDUCTOR-- after SENSOR Signed and Sealed this  
Third Day of June, 2025

Coke Morgan Stewart  
*Acting Director of the United States Patent and Trademark Office*